United States Patent
Ferrante et al.

(12)

(10) Patent No.: US 6,262,119 B1
(45) Date of Patent: Jul. 17, 2001

(54) METHODS OF TREATING IMMUNOPATHOLOGIES USING POLYUNSATURATED FATTY ACIDS

(75) Inventors: Antonio Ferrante, Mount Osmond; Alfred Poulos, Kensington Gardens; Michael Joseph Pitt, Gordon; Christopher John Easton, Weetangera; Merilyn Joy Sleigh, Neutral Bay; Deborah Ann Rathjen, Sheidow Park; Fred Widmer, Ryde, all of (AU)

(73) Assignees: Peptide Technology Limited, New South Wales; Women's and Children's Hospital Adelaide, North Aldelaide, both of (AU)

( * ) Notice: Subject to any disclaimer, the term of this patent is extended or adjusted under 35 U.S.C. 154(b) by 0 days.

(21) Appl. No.: 09/171,095

(22) PCT Filed: Apr. 14, 1997

(86) PCT No.: PCT/AU97/00231

§ 371 Date: Apr. 12, 1999

§ 102(e) Date: Apr. 12, 1999

(87) PCT Pub. No.: WO97/38688

PCT Pub. Date: Oct. 23, 1997

(30) Foreign Application Priority Data

Apr. 12, 1996 (AU) .................................................. PN 9250
Apr. 26, 1996 (AU) .................................................. PN 9538

(51) Int. Cl.$^7$ ..................................................... A61K 31/20
(52) U.S. Cl. .......................... 514/560; 514/627; 514/826; 514/861; 514/863; 514/885; 514/903
(58) Field of Search ...................................... 514/627, 560, 514/826, 861, 863, 885, 903

(56) References Cited

U.S. PATENT DOCUMENTS

| | | | |
|---|---|---|---|
| 5,585,400 | 12/1996 | Cook et al. | 514/560 |
| 5,616,607 | 4/1997 | Pace-Asciak et al. | 514/560 |
| 5,618,955 | * 4/1997 | Mechoulam et al. | 554/66 |
| 5,998,476 | * 12/1999 | Sleigh et al. | 514/560 |

FOREIGN PATENT DOCUMENTS

| | | |
|---|---|---|
| 0582834 | 2/1994 | (EP) . |
| WO 93/00326 | 1/1993 | (WO) . |
| WO 96/05164 | 2/1996 | (WO) . |
| WO 96/11908 | 4/1996 | (WO) . |
| WO 96/13507 | 5/1996 | (WO) . |

* cited by examiner

*Primary Examiner*—Frederick Krass
(74) *Attorney, Agent, or Firm*—Nixon & Vanderhye

(57) ABSTRACT

Method of treating or ameliorating symptoms of T-cell mediated disease wherein a composition comprising a therapeutically effective amount of a polyunsaturated fatty acid and a pharmaceutically acceptable carrier is administered to the patient. The polyunsaturated fatty acid contains 18–25 carbon atoms, 1–6 double bonds and has 1 or 2 substitutions selected from β oxa, γ oxa, β thia and γ thia, based on the fatty acid acyl carbon atom, or the polyunsaturated fatty acid contains 16–26 carbon atoms, 3-double bonds and is covalently coupled at the carboxylic acid group to an amino acid.

13 Claims, 11 Drawing Sheets

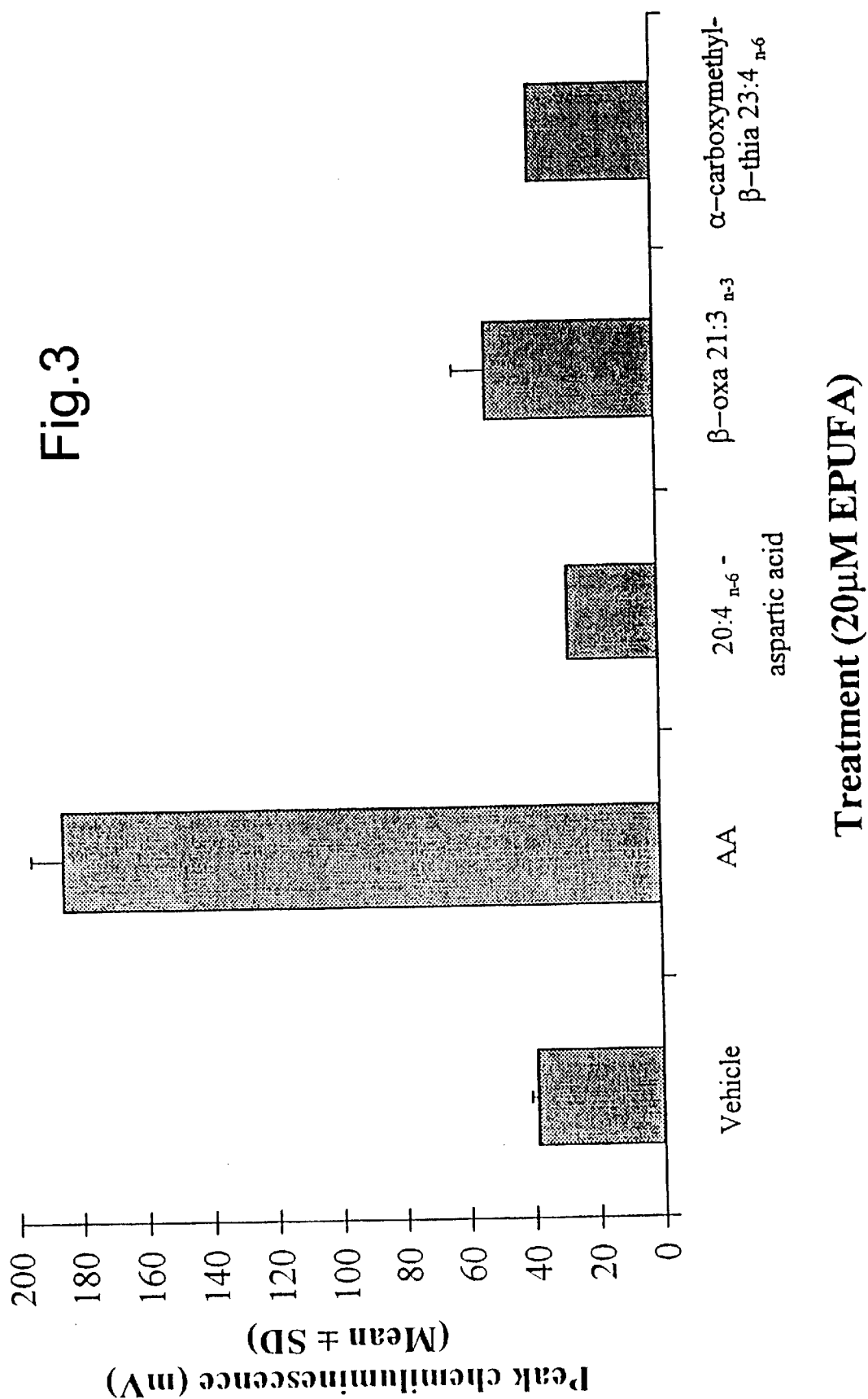

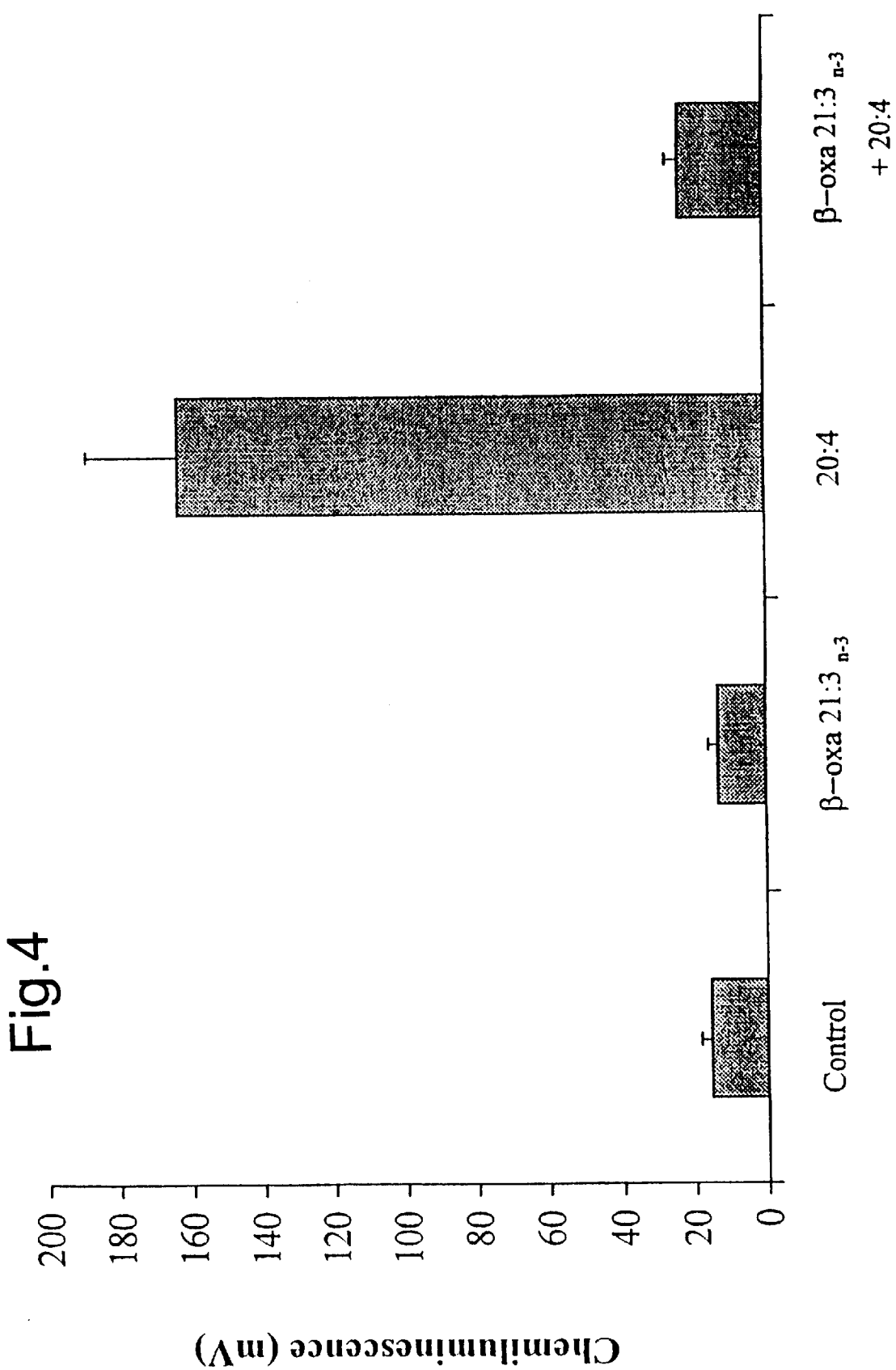

METHODS OF TREATING IMMUNOPATHOLOGIES USING POLYUNSATURATED FATTY ACIDS

This application is a 371 of PCT/AU97/00231, filed Apr. 14, 1997.

The present invention relates to methods of treatment of a variety of disease states involving the use of new polyunsaturated fatty acids which include at least one β oxa, β thia, γ oxa or γ thia substitution and/or which includes an amino acid. The disease states include multiple sclerosis, rheumatoid conditions, and other T-cell mediated diseases; allergic conditions such as asthma, allergic rhinitis, contact hypersensitivity; transplant rejection and graft vs. host disease and conditions where arachidonic acid metabolites are formed.

BACKGROUND OF THE INVENTION

Multiple sclerosis (MS) is a chronic demyelinating disease of the central nervous system and is the commonest chronic neurological disease of young adults. The incidence of MS and its pattern of distribution have been unchanged for decades. The disease remains essentially untreatable.

MS usually affects multiple areas of white matter in the central nervous system (CNS), most frequently, the preventricual white matter, brain stem, spinal cord and the optic nerves. The primary process destroys myelin sheaths and eventually kills oligodendrocytes creating the characteristic plaque of MS.

The early development of the plaque is characterised by the development of perivascular inflammation followed by the migration of lymphocytes, plasma cells and macrophages into the lesion. This is followed by astrocyte gliosis and the attempts of demyelination by oligodendrocytes. The plaque is surrounded by lymphocytes.

Although the aetiology of MS is still unknown, the focus of research efforts that have led to plausible hypotheses have been those of immune dysregulation including autoimmunity and genetic predisposition, both of which may play a role in he actual development of disease. Both TNFβ (lymphotoxin) and TNFα are thought to play a role in the pathophysiology.

Multiple immunological abnormalities are reproducibly found in patients in the acute stage of the disease. The synthesis of immunoglobulins, although normal in the periphery, is increased in the central nervous system and the antibodies produced have a characteristic banding pattern. The antigenic specificity of these antibodies is not known and it is unclear whether they have a role to play in the progression of the disease.

Various stressors known to activate the immune system such as viral infection or surgery can also produce an exacerbation of MS. Other activator such as γ-interferon produce similar effects when administered. In addition, immunosuppressive anti-inflammatory therapy with corticosteroids for example, can produce modest remission or at lease palliation for short periods of time, although this therapy is controversial.

Lymphocyte reactivity against two neuronal antigens, myelin basic protein and proteolipid has been demonstrated. Although not proven, this activity would form the basis for an auto-immune response against neuronal tissue.

Myelopathy, a disorder of the spinal cord, can have many different aetiologies, most of which are mediated by inflammation, including the following:

Neurosyphillis;

$b_{12}$ or folate deficiency;

sarcoidosis;

transverse myelitis;

arachidonitis;

cervical spondylitis;

motor neuron disease;

neurofibromatosis;

spinal cord compression from tumour, disc or arthritis;

lupus erythematosus of the spinal cord; and viral encephalomyelitis

Chronic inflammation or, as more commonly known, chronic immune system activation occurs in response to persistent antigen whose origin may be exogenous or may result from an auto-immune state. Such chronic inflammation results in local tissue destruction and depending upon the type of inflammation can result in systemic effects due to the sustained production of inflammatory mediators. Such inflammatory mediators include the cytokines which are soluble mediators produced by activated lymphocytes and macrophages and effect cellular communication and physiological response. Chronic immune activation can occur as a result of infectious disease, such as chronic fatigue syndrome or toxic shock syndrome or through auto-immune mechanisms resulting in such conditions as rheumatoid arthritis, inflammatory bowel disease, Crohns Disease and other diseases such as graft versus host disease.

Rheumatoid arthritis (Marrow et al, I "Auto-immune Rheumatic Disease", *Blackwell Scientific Publ.* Oxford, UK, Chapter 4 pp148–207 (1987) is a disease characterised by chronic inflammation and erosion of joints that may affect up to 3% of the population, including children. Symptoms of rheumatoid arthritis include morning stiffness, swelling and pain upon motion in at lease one joint and joint swelling. Non-specific symptoms including lethargy, anorexia and weakness as well as fever and lymphadenopathy (characteristic of immune activation) may antedate joint involvement. Extra-articular manifestations of rheumatoid arthritis include vasculitis, cataracts, uveitis, interstitial fibrosis, pericarditis and myocarditis, peripheral neuropathy, myeloid deposits, chronic anaemia and subcutaneous and pulmonary nodules.

Genetic factors and infectious agents including bacteria, fungi, mycoplasmas and viruses have been associated with the development of rheumatoid arthritis. Mild rheumatoid arthritis may be treated with non-steroidal anti-inflammatory drugs while severe cases require systemic corticosteroids, anti-metabolites or cytotoxic agents. Experimentally, anti-CD4 monoclonal antibodies and anti-TNFα antibodies have been used to treat rheumatoid arthritis (Horneff et al, Cytokine 3 266–267 (1991); Horneff et al, Arth. Rheum. 34 129–140 (1991) and Shoenfeld et al, Clin. Exp. Rheum. 9. 663–673 (1991), Williams et al, 1992 PNAS 89, 9784).

Arthritis is the most common manifestation of systemic lupus erythematosus (SLE) and is classically the symptom for which the patient seeks medical attention. SLE is a set of clinical disorders involving multiple organ systems and characterised by the production of auto-antibodies and immune complexes. The immune complexes are deposited in various organs eg kidney, gastrointestinal tract and the resultant inflammation and tissue injury cause cell and organ dysfunction. B cell hyper-reactivity and production of auto-antibodies is an attributed imbalance between CD8 and CD4 T cells and altered cytokine production including increased production of interleukini 1, interleukin 2 and interferon γ. Azathioprine is commonly used in management of the disease.

Systemic sclerosis (scleroderma) is characterised by thickening and fibrosis of the skin and by distinctive forms of internal organ involvement. (Claman, H. N., 1989, JAMA 262: 1206). The skin thickening of scieroderma is due to the accumulation of collagen in the lower dermis. The immobility of the skin is caused by replacement of the subcutaneous tissue with fibrous bands. Dermal fibroblasts obtained from involved skin accumulated types I, III and IV collagen, fibronectin and glycosaminoglycan. This is a secondary response to factors released by other cells. T-helper cells are demonstrable in involved skin. Elevated levels of serum IL-2 and IL-2 receptor are present and correlate with clinical progression of the disease (Kahaleh et al, 1989. Ann. Itern. Med. 110:446). This suggests a role for lymphokines that either stimulate collagen biosynthesis in fibroblasts or stimulate other cells such as monocytes or mast cells to produce such factors. Human chronic graft vs host disease is associated with a similar dermal fibrotic change. Interferon $\gamma$ is known to stimulate collagen accumulation by systemic scleroderma fibroblasts.

Polymyositis is a chronic inflamniatory disease of skeletal muscle, characterised by symmetric weakness of proximal limb girdle muscles and muscles of the trunk, neck and pharynx. A characteristic rash may also be present (Hochberg et al, 1986, Semin Arthritis Rheum 15:168). Peripheral blood lymphocytes from patients with polyinyositis produce lymphokines cytotoxic to foetal muscle cells in vitro. In addition, the proportion of activated lymphocytes is increased particularly in muscle tissue. Environmental factors, particularly infectious agents (influenza B1, cocksackie virus B. *Toxoplasma gondii*), may be involved in the pathogenic process, Many drugs have been implicated in chronic inflammatory myopathy, including D-penicillamine, colchanicine, and ethanol.

Leukoclastic vasculitis (Laken and Smiley, 1981, Dis Mon. 64:181) is the name given to the pathologic lesions seen in the blood vessels that produce palpable purpura. It is thought that the lesions are produced by the interaction of cells and humoral products. The putative antigen (arising from streptococcal infection or drug interaction ) reacts with IgE attached to the surface of mast cells. The activated mast cells release factors (PAF, prostaglandins, leukotrienes) causing activation of platelets and release of vasoactive amines responsible for dilation and oedema in post capillary venules. Neutrophils migrate to the site, releasing toxic granule contents resulting in fibrinoid necrosis, extravasation of the red blood cells, and then to clinically apparent lesions of palpable purpura. In a related condition, Panniculitis, there is also inflammation of fatty tissue. There are two types of Panniculitis, septal and lobar. Among the septal forms, Behscets Disease may be a cause of erythema nodosum.

Inflammatory bowel disease (IBD) and Crohns disease are chronic inflammatory conditions that fulfil some of the criteria of an auto-immune disease (Snook, Gut 31 961–963 (1991)). Inflammation and tissue damage involves the recruitment and activation of neutrophils, macrophages and lymphocytes (MacDermott et al, Adv. Immunol. 42 285–328 (1988)) which generate cytokines and proinflammatory molecules such as prostaglandins and leukotrienes (MacDermott, Mt. Sinai J. Med. 57 273–278 (1990)). As a result of chronic activation of immunocompetent cells, IL-1, IL-6 (Starter, Immunol. Res. 10 273–278 (1990); Fiocchi, Immunol. Res. 10 239–246 (1991)) and TNFα (MacDermott, Mt. Sinai J. Med. 57 273–278 (1990)) are all elevated in IBD and Crohins Disease patients.

Drugs used to treat IBD and Crohns Disease include anti-inflammatory agents such as sulphasalazine (5-ASA) corticosteroids, cyclosporin A and azathiprine (Hanauer, Scand, J, Gastroenterol. 25 (Supl. 175) 97–106 (1990); Peppercorn, Annal. Intern. Med. 112 50–60 (1990)). Experimentally, anti-CD4 and anti-TNF monoclonal antibodies have been used to successfully treat ulcerative colitis (Emmerich et al, Lancet 338 570–571 (1991)).

Transplanted organs and tissues may be rejected when host T cells come in contact with donor HLA molecules. The process of rejection involves several effector mechanisms including cytotoxic T cells, lymphokines (principally TNFcc, IL-1, IL-2 and interferon y) and other soluble mediators of inflammation (eg prostaglandins and leukotrienes). Immunosuppressive drugs (eg azathrioprine, cortocisteroids, cyclosporine A, FK506, and polyclonal and monoclonal antibodies) inhibit T cell proliferation and production of cytokines in attempting to prolong graft survival.

Whilst a host may react against a genetically incompatible graft producing a host-versus-graft response, an immunocompetent graft (such as bone marrow or intestinal tissue) may react against the host resulting in graft-versus-host disease. These reactions are mediated by allogenic responses directed against a foreign MEC molecule and are mimicked in vitro by the mixed lymphocyte reaction (MLR). Graft/host interactions result in chronic inflammation surrounding the grafted tissue with an increase in markers of immune activation such as are seen in AIDS (Grant, Immunol. Today 12 171–172 (1991)). Treatment of the graft/host interactions currently include either azathioprine, cyclosporin A or methylprednisone and, more recently, rapamycin (Spekowski et al, Transplantation 53 258–264 (1992); Huber et al, Bibliotheca Cardiologica. 43 103–110 (19883). Monoclonal antibodies specific for CD3 (Wissing et al, Clin Exp Immunol. 83 333–337 (1991)), CD4 (Reinke et cd, Lancet 338 702–703 (1991)) and TNFα have been used experimentally to inhibit graft/host reactions.

Immediate hypersensitivity occurs after the binding of antigen to preformed antibodies of the IgE isotype bound to Fc receptors in mast cells or basophils. This binding leads to rapid degranulation and release of inflammatory mediators that act on tissues. The production of IgE is stimulated by T lymphocytes and their products (cytokines), mainly by interleukin 4 in synergy with interleukin 5, together with interleukin 6 and TMF produced by macrophages. Asthma, triggered by inhalant allergens, is an IgE mediated disease. Allergic rhinitis is an IgE-mediated inflammatory disease involving the nasal membranes. As many as 80% of patients with allergic asthma have coexistent symptoms of allergic rhinitis, and at least 40% of patients with allergic rhinitis manifest asthma at some time. In these conditions mast cells release histamine, leukotrienes such as $LTB_4$, $C_4$, $D_4$ and $E_4$, prostaglanidin $D_2$ and proteases which are thought to be responsible for the immunopathology including an inflammatory infiltrate comprised largely of eosinophils. The presence of large numbers of neutrophils are also characteristic of asthmatic tissue.

Although the pathogenesis of atopic dermatitis is poorly understood, the frequent co-incidence of atopic dermatitis and allergic rhinitis or asthma suggests an immediate hypersensitivity may be involved. Serum IgE levels are frequently elevated in patients with atopic dermatitis and often decrease during periods of remission. Topical corticosteroid preparations are used during acute episodes and may be needed chronically in some patients. As a consequence, during exacerbations of eczema, patients frequently develop secondary bacterial infections.

Allergic contact dermatitis is a clinically important example of a delayed type hypersensitivity reaction which is T cell mediated involving release of T cell derived cytokines and proliferation of T cells within the skin. Other inflammatory cells, macrophages, lymphocytes, basophils, mast cells and eosinophils are also recruited to the involved area by cytokines and chemoattractants. Frequent contact sensitisers include Rhus antigen (found in poison ivy and oak), parapheylenediamine, nickel, rubber compounds, ethylenediamine, certain local anaesthetics (eg benzocaine), chromate and neomycin. Steroids, including prednisone, are employed for widespread contact dermatitis.

Psoriasis (Anderson and Voorhees, Psoriasis, In: Thiers, Dobson eds. Pathogenesis of skin disease. New York. Churchill Livingstone, 1986: 67) is a primary disease of the skin characterised bv well demarcated, inflammatory papules and plaques, which are typically covered by thickened scales. Neutrophils are found in psoriatic lesions. It is likely that arachidonic acid, levels of which are much higher than normal in psoriatic plaques, and its metabolites are important in this aspect of the disease. Further drugs which block the cyclo-oxygenase pathway of arachidonic acid metabolism (eg non-steroidal anti-inflammatory drugs such as indomethacin, phenylbutazone, meclotenamate) induce exacerbations of psoriasis. Dramatic clearing of recalcitrant, severe psoriasis has been achieved using cyclosporin A. The major mechanism of action of cylcosporin A is to inhibit the release of lymphokines produced by activated T lymphocytes. Thus it has been hypothesised that the activated T cells, in response to autologous or exogenous antigens, release factors that directly result in inflammation and epidermal proliferation, or indirectly produce these effects by activating macrophages or keratinocytes which then release cytokines, mediators of inflammation or growth factors that can elicit the pathology of psoriatic plaques.

Inflammation may be caused by bacteria, viruses and /or other infective agents, opportunistic infections (which may be consequent on an immunodepressed state, for example resulting from cancer or therapy, particularly cytotoxic drug therapy or radiotherapy), auto-immunity or otherwise. Septic shock is an illustration of a disease involving inflammation. Many of the clinical features of Gram-negative septic shock may be reproduced in animals by the administration of LPS to animals can prompt severe metabolic and physiological changes which can lead to death.

Associated with the injection of LPS is the extensive production of pro-inflammatory cytokines such as tuinour necrosis factor alpha (TNFα).

Cachexia, which is characteristic of chronic exposure to TNF or interleukin-6, is a common symptom of advanced malignancy and severe infection. It is characterised by abnormal protein and glucose metabolism and body wasting. Chronic administration of TNF IL-1 in mice, rats and/or humans cause anorexia, weight loss and depletion of body lipid and protein within 7 to 10 days (Cerami et al, 1985, Immunol. Lett, 11, 173: Fong et al, 1989 J. Exp. Med. 170, 1627. Moldawer et al, Am. J. Physiol., 254 G450–G456, 1988; Fong et am, Am. J Physiol. 256, R659–R665 (1989); McCarthy et al, Am. J. Clin. Nature. 42, 1179–1182. 1982). TNF levels have been measured in patients with cancer and chronic disease associated with cachexia.

TNFα and IL-1, with their common functional activities such as pyrogenicity, somnogenicity and being mediators of inflammation, have been implicated in the pathology of other diseases associated with chronic inflammation apart from toxic shock and cancer-related cachexia. TNF has been detected in synovial fluid in patients with both rheumatoid and reactive arthritis and in the serum of patients with rheumatoid arthritis (Saxne et al, 1988. Arthrit. Rheumat, 31, 1041). Raised levels of TNF have been detected in renal transplant patients during acute rejection episodes (Maury and Teppo 1987, J. Exp. Med. 166, 1132). In animals, TNF has been shown to be involved in the pathogenesis of graft-versus-host disease in skin and gut following allogenic marrow transplantation. Administration of a rabbit anti-murinie TNF antibody was shown to prevent the histological changes associated with graft-versus-host disease and to reduce mortality (Piquet et en, 1987, J. Exp. Med. 166, 1220). TNF has also been shown to contribute significantly to the pathology of malaria (Clark et al, 1987, Am. J. Pathol. 129, 192–199). Further, elevated serum levels of TNF have been reported in malaria patients (Scuderi et al, 1986, Lancet 2, 1364–1365).

PUFAs are known to have a range of useful biological activities (see for example International Patent Application Nos. WO 93/00084 and WO 95/00607 and the references cited therein). Unfortunately, due to their limited stability in vivo, PUFAs have not achieved widespread use as therapeutic agents. The present inventors have found that PUFAs including at least one β oxa, β thia, γ oxa or γ thia substitution have activity in a number of in vitro systems which suggest that these PUFAs may be useful in treatment of a range of disease states. In addition, the present inventors have developed substituted PUFAs which while retaining biological activity have increased stability in vivo ie slower metabolic turnover. The conjugation of an amino acid to PUFA also increases solubility of the compound.

The present inventors have also found that certain of the amino acid coupled PUFA suppress cytokine production and inhibit inflammation in response to carageenan and delayed type hypersensitivity to sheep red blood cells. Such compounds have utility in the treatment of T cell-mediated diseases, autoimmune disease, transplant rejection, graft vs host disease and allergic disease.

While saturated β oxa fatty acids can be obtained using the standard procedure for ether synthesis, by reaction of alkyl halides with dianions of α-hydroxy acids or by treating α-halo acids with deprotonated alcohols, the unsaturated β-oxa fatty acids of the present invention are not accessible using normal methods. Attempts to obtain the unsaturated compounds in this manner lead only to decomposition products, resulting from undesirable side reactions at the olefinic and allylic carbons.

In a recent variation of the standard procedure, saturated β-oxa fatty acids have been obtained through nucleophilic substitution reactions under less vigorous conditions, by treating diazoacetates, activated by complexation with boron trifluoride etherate, with alcohols. However, boron trifluoride etherate is known to cause isomerization of alkenes and it is therefore unsuitable for use in the synthesis of unsaturated β-oxa fatty acids.

As disclosed in co-pending International Patent Application No PCT/AU95/00677 (the disclosure of which is incorporated herein by cross reference) it has been found that unsaturated β-oxa fatty acids can be obtained in good yields, by insertion of carbenes in the O—H bond of alcohols. There is no complication from other carbene insertion reactions and, of particular significance, the olefinic moieties are inert under the reaction conditions.

The carbene can be generated from the corresponding diazo acetate or diazo alkane, by treatment with a catalyst such as a rhodium salt. Reaction of the carbene with the complementary alcohol, which is either a derivative of α-hydroxy acetic acid or an unsaturated fatty alcohol affords the unsaturated β-oxa fatty acid. In a preferred embodiment of the alcohols are those obtained by reduction of naturally occurring unsaturated fatty acids or the corresponding exters, and reaction with an ester of diazo acetic acid affords the unsaturated β-oxa fatty acid.

It has also been shown that both β-oxa and β-thia substituted fatty acids are unable to undergo 1 oxidation. In addition, certain of these compounds display other properties which differ from those of natural PUFA including enhanced solubility, varied oxidation reduction potentials and different charge and polarity.

SUMMARY OF THE INVENTION

Accordingly, in a first aspect the present invention consists in a method of treating or ameliorating the symptoms of multiple sclerosis in a subject, the method comprising administering to the subject a composition comprising a therapeutically effective amount of a polyunsaturated fatty acid and a pharmaceutically acceptable carrier; in which the polyunsaturated fatty acid contains 18–25 carbons, 1–6 double bonds and has one or two substitutions selected from the group consisting of , oxa, γ oxa, β thia and γ thia, or the polyunsaturated fatty acid contains 16–26 carbon chain, 3–6 double bonds and is covalently coupled at the carboxylic acid group to an amino acid.

In a second aspect the present invention consists in a method of treating or ameliorating the symptoms of rheumatoid arthritis or other rheumatoid-like condition such as lupus in a subject, the method comprising administering to the subject a composition comprising a therapeutically effective amount of a polyunsaturated fatty acid and a pharmaceutically acceptable carrier; in which the polyunsaturated fatty acid contains 18–25 carbons. 1–6 double bonds and has one or two substitutions selected from the group consisting of β oxa, γ oxa, β thia and γ thia, or the polyunsaturated fatty acid contains 16–26 carbon chain. 3–6 double bonds and is covalently coupled at the carboxylic acid group to an amino acid.

In a third aspect the present invention consists in a method of treating or ameliorating the symptoms of T-cell mediated disease in a subject, the method comprising administering to the subject a composition comprising a therapeutically effective amount of a polyunsaturated fatty acid and a pharmaceutically acceptable carrier; in which the polyunsaturated fatty acid contains 18–25 carbons, 1–6 double bonds and has one or two substitutions selected from the group consisting of β oxa, γ oxa, β thia and γ thia, or the polyunsaturated fatty acid contains 16–26 carbon chain, 3–6 double bonds and is covalently coupled at the carboxylic acid group to an amino acid.

Examples of T-cell mediated diseases include allergic diseases, such as vasculitis, allergic contact dermatitis and contact dermatoconjunctivitis, chronic inflammatory diseases, such as Crohn's disease, inflammatory bowel disease and polymyositis, recurrent inflammatory disease such as herpes simplex stromal keratitis, and transplant rejection, graft vs. host and autoimmune diseases such as scleroderma, rheumatoid arthritis and multiple sclerosis.

In a fourth aspect the present invention consists in a method of treating or ameliorating the symptoms of a disease state involving elevated levels of products of arachidonic acid metabolism in a subject, the method comprising administering to the subject a composition comprising a therapeutically effective amount of a polyunsaturated fatty acid and a pharmaceutically acceptable carrier; in which the polyunsaturated fatty acid contains 18–25 carbons, 1–6 double bonds and has one or two substitutions selected from the group consisting of β oxa, γ oxa, β thia and γ thia, or the polyunsaturated fatty acid contains 16–26 carbon chain, 3–6 double bonds and is covalently coupled at the carboxylic acid group to an amino acid.

Examples of diseases in which products of arachidonic acid play a pathological role include psoriasis, allergic asthma and rhinitis, leukoclastic vascultis, urticaria and angioedema.

In a preferred embodiment of the present invention the polyunsaturated fatty acid is a polyunsaturated fatty acid which contains 18–25 carbons, 1–6 double bonds and has one or two substitutions selected from the group consisting of β oxa, γ oxa, β thia and γ thia. It is further preferred that this polyunsaturated fatty acid includes a further substitution selected from the group consisting of hydroxy, hydroperoxy, peroxy and carboxymethyl substitutions. In another embodiment the substituted fatty acid is covalently attached to an amino acid, preferably glycine or aspartic acid. In yet another preferred form of this embodiment of the present invention the polyunsaturated fatty acid has a co hydroxy substitution.

In a further preferred embodiment of the present invention the polyunsaturated fatty acid compound contains 20–25 carbon atoms and 3–6 double bonds and is preferably an n-3 to n-6 fatty acid.

In another preferred embodiment of the present invention, the polyunsaturated fatty acid is 21 carbons with 3–4 double bonds containing a β oxa or β thia substitution, 22 carbon atoms with 3–4 double bonds containing a γ thia or β oxa substitution, 23 carbons with 3–4 double bonds containing a β thia substitution, 24 carbons with atoms with 3–4 double bonds containing a γ thia substitution 25 carbons with 306 double bonds containing a β oxa substitution, 25 carbons with 3–6 double bonds containing a β this substitution, or 23 carbons, 3–6 double bonds, β thia and α-carboxymethyl group.

In yet another preferred embodiment of the present invention the polyunsaturated fatty acid is a polyunsaturated fatty acid which contains 16–26 carbon chain, 3–6 double bonds and is covalently coupled at the carboxylic acid group to an amino acid. It is also preferred that the amino acid is glycine or aspartic acid.

In a still further preferred embodiment of the present invention, the polyunsaturated fatty acid compound is γ-linolenic acid-glycine, α-linolenic acid-glycine, arachidonic acid-glycine, docosahexaenoic acid-glycine, eicosapentaenioic acid-glycine, γ linolenic acid-aspartic acid, α-linolenic acid-aspartic acid, arachidonic acid-aspartic acid, eicosapentaenoic acid-aspartic acid or docosahexaenoic acid-aspartic acid.

BRIEF DESCRIPTION OF THE DRAWINGS

In order that the nature of the present invention may be more clearly understood preferred forms thereof will now be described with reference to the following examples and Figures in which:

FIG. 3 shows the effect of novel PUFA 20:4—aspartic acid, Poxa 21:3n-3 and α carboxymethyl β thia 23:4n-6 on neutrophil cheiniluminescence.

FIG. 4 shows the effect of β oxa 21:3n-3 on the arachidonic acid-induced chemiluminescence response.

DETAILED DESCRIPTION OF PREFERRED EMBODIMENTS

Methods

Mononuclear Cell Proliferation Assays

Figure 1A:
FIG. 1a shows Arachidonic acid 5,8,11,14-Eicosatetraenoic acid.
Figure 1B:
FIG. 1b shows 5-Hydroperoxy-6E, 8X, 11Z, 14Z-Eicosatetraenoic acid
Figure 1C:
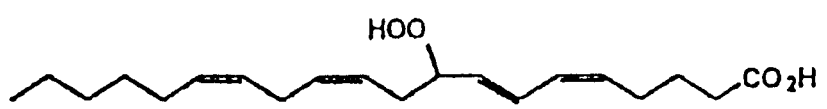
FIG. 1c shows 9-Hydroperoxy-5Z, 7E, 11Z, 14Z-Eicosatetraenoic acid
Figure 1D:
FIG. 1d shows 8-Hydroperoxy-5Z, 9E, 11Z, 14Z-Eicosatetraenoic acid
Figure 1E:
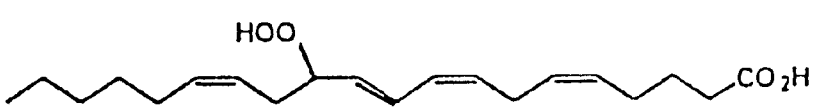
FIG. 1e shows 12-Hydroperoxy-5Z, 8Z, 10E, 14Z Eicosatetraenoic acid
Figure 1F:
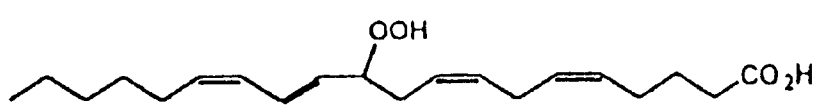
FIG. 1f shows 11-Hydroperoxy-5Z, 8Z, 12E, 14Z Eicosatetraenoic acid.
Figure 1G:
FIG. 1g shows 15-Hydroperoxy-5Z, 8Z, 11Z, 13E Eicosatetraenoic acid.
Figure 1H:
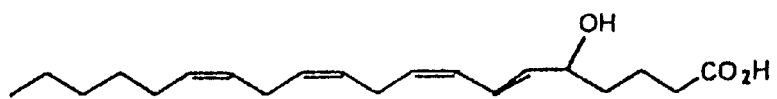
FIG. 1*h* shows 5-Hydroperoxy-6E, 8Z, 11Z, 14Z-Eicosatetraenoic acid.
Figure 1I:
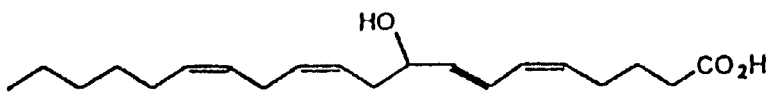
FIG. 1*i* shows 9-Hydroperoxy-5Z, 7E, 11Z, 14Z Eicosatetraenoic acid.
Figure 1J:
FIG. 1*j* shows 8-Hydroperoxy-5Z, 9E, 11Z, 14Z-Eicosatetraenoic acid.
Figure 1K:
FIG. 1*k* shows 12-Hydroperoxy-5Z, 8Z, 10E, 14Z Eicosatetraenoic acid.
Figure 1L:
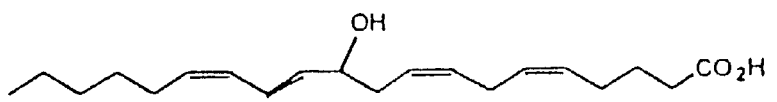
FIG. 1*l* shows 11-Hydroperoxy-5Z, 8Z, 12E, 14Z Eicosatetraenoic acid.

Mononuclear cells were separated from peripheral blood of normal human donors as described by Ferrante and Thong (1980, *J. Immunol. Methods* 36:109)). The mononuclear cells were resuspended in RPMI-1640 containing 20% human AB serum and placed into 96 well microtrays (50 μl per well, cell density 4×10$^6$ cells/ml). Fatty acid (66pmn) was then added in 50ul and pre-incubated with the cells for 30 min at 37° C. in 5% $CO_2$. Mitogen (PHA, ConA, PWM, *Staph. aureus*) was then added in 100 μl and the cells incubated for 66 hours at 37° C. in 5% $CO_2$ before the addition of tritiated thymidine (1 μCi/well). After a total of 72 h in culture the cells were harvested and proliferation (thymidine incorporation) and supernatant's assayed for the presence of cytokines.

Cytokine Assays

Cytokine levels in culture supernatants were determined by specific ELISA using anti-cytokine antibodies. The following cytokine levels were determined TNFα, TNFβ, interferon-γ, IL-1β, IL-2.

Delayed Type Hypersensitivity Against Sheep Red Blood Cells.

Female balb/c mice were administered a priming dose of 100 μl of a 10% haematocrit of sheep red blood cells (SRBC) subcutaneously. Six days later mice were administered 25 μl of a 10% haematocrit of SRBC intradermally into the right hind footpad at time T-0 hrs. The subsequent anti-inflammatory response was evaluated by measuring the thickness of both hind footpads. Standard anti-inflammatory compounds, vehicle and test substances were administered intraperitonieally one hour prior to the SRBC challenge. PUFA compounds were administered in peanut oil.

Leukotriene B4 Production in Neutrophils.

5×10$^6$ human neutrophils were incubated with test compounds, NDGA or Zileuton 10–15 mins at 37° C. Calcium ioniophore (A23187, 5 μM) was added and the incubation proceeded for a further 30 mins. The incubated mixture was cooled in an ice bath for 3 mins prior to centrifugation at 10,000 rpm at 4° C. for 10 min. The supernatant was then collected and aliquots stored frozen at −20° C. $LTB_4$ levels were determined by ELISA using the Amersham kit and according to the manufacturers instructions.

Carageenan-Induced Paw Oedema:

Female BALB/c mice were administered 25 μl of a 1% solution of carageenan (Sigma Chemical Company) into the right hind footpad. Test substances were administered ip one hour prior to the administration of carrageenan. The subsequent inflammatory response was evaluated by measuring the thickness of both hind footpads.

Neutrophil Chemiluminescence:

Neutrophils were prepared from the blood of healthy volunteers. Freshly collected blood was layered onto a Hypaque-Ficoll medium of density 1.114 and centrifuged at 400 g for 30 minutes at room temperature. After centrifugation the leukocytes resolved into two distinct bands, with neutrophils being present in the second band (Ferrante and Thong, 1982, *J. Immunzol. Metiods.* 48:81–85). Activation of neutrophils was measured by lucigenin-dependent chemiluminescence following a 10 minute incubation of test compound (20 μM final) with 1×10$^6$ neutrophils (Kumaratilake et al. 1990. *Clin. Exp. Immuizol.* 80:257–262).

Chemical Synthesis $$ROH + N_2{=}CHCO_2tBu \xrightarrow{Rh_2(OAc)_4}_{CH_2Cl_2, RT} ROCH_2CO_2t\text{-}Bu$$
$$1 \quad\quad 2 \quad\quad\quad\quad\quad\quad\quad\quad 3$$

$$\Big\downarrow \begin{array}{l} CF_3CO_2H \\ CH_2Cl_2, RT \end{array}$$

$$ROCH_2CO_2H$$
$$4$$

a: R=$CH_3(CH_2)_4(CH^{cis}{=}CHCH_2)_4(CH_2)_3$— b: R=$CH_3(CH_2)_4(CH^{cis}{=}CHCH_2)_3(CH_2)_4$— c: R=$CH_3CH_2(CH^{cis}{=}CHCH_2)_3(CH_2)_7$— d: R=$CH_3CH_2(CH_{cis}{=}CHCH_2)_6(CH_2)_2$— e: R=$CH_3CH_2(CH_{cis}{=}CHCH_2)_4(CH_2)_5$—

Reagents

Arachidonyl Alcohol (1a)—Nu Chek Prep., Elysian, Minn., USA

Gamma Linolenyl Alcohol (1b)—Nu Chek Prep., Elysian, Minn., USA

Linolenyl Alcohol (1c)—Nu Chek Prep., Elysina, Minn., USA

Docosahexaenyl Alcohol (1d)—Nu Chek Prep., Elysian, Minn., USA 6, 9, 12, 15-Octadecatetraeniyl alcohol (1e)—Synthesised by lithium alumiiniium lhydride reduction of Methyl 6, 9, 12, 15-Octadecatetraenoate.

Methyl 6, 9, 12, 15-Octadecatetraeiioate—Sigma Chemical Company

Thodium Acetate Dimer—Aldrich Chemical Company tert-Butyl DiazoAcetate (2)—synthesized from tert-Butyl Acetoacetate as per:

Regitz, M; Hocker, J; Leidhegener, A. *Organic Syntheses* Coll. Vol. 5. 179.

Tert-Butyl Acetoacetate—Fluka AG

Trifluoroacetic Acid—Aldrivch Chemical Company.

All solvents were distilled prior to use, except for diethyl ether (ether) which was Ajax Chemicals analytical grade and was used without further purification.

Column chromatographies were performed under positive nitrogen pressure on Merck Silica Gel 60 (230–400 mesh), Art, 9385.

Procedure ter-Butyl alkyloxyacetates 3

The relevant fatty alcohol 1 (1 mol equivalent) was weighed into a two-neck round bottom flask under dry nitrogen and was dissolved in dichloromethane. To this stirred solution was added rhodium acetate dimer (0.5 mol %), followed by the dropwise addition of a solution of tert-butyl diazoacetate 2(2.5 mol equivalents) in dichloroinethane via syringe. After the addition was complete the reaction mixture was stirred at toom temperature under nitrogen for 2 hrs. The crude reaction mixture was concentrated under a stream of dry nitrogen and the residue was purified by flash column chromatography on silica, eluting with hexane/diethyl ether (9:1), to afford the relevant tert-butyl alkloxyecetate 3 as an oil.

Alkyloxyacetic Acids 4

The relevant tert-butyl alkyloxyacetate 3 (ca. 100 mg, 1 mol equivalent) was weighed into a two-neck round-bottom flask under dry nitrogen and was dissolved by the addition of dichloromethane (ca. 4 ml). To this stirred solution was added trifluoroacetic acid (ca. 1 ml), and the reaction mixture was stirred at room temperature under nitrogen for 2 hrs. The crude reaction mixture was concentrated under stream of dry nitrogen and the residue was purified by flash column chromatography on silica, eluting with hexane/diethly ether/acetic acid (40:60:2), to afford the relevant alkyloxyacetic acid 4 as an oil.

t-Butyl (5, 8, 11, 14-eicosatetraenyloxy) acetate (3a) [t-Bu β-oxa 23:4 (n-6)]

$^1$H n.m.r. (200 mnz, CDCl$_3$) δ 0.89 (3H, t, J 6.7 Hz, C20'—H$_3$, 1.25–1.38 (8H, m, C3'—H$_2$, C17'—H$_2$, C18'—H$_2$, C19'—H$_2$), 1.49 (9H, s, C(CH$_3$)$_3$), 1.56–1.69 (2H, m, C2'—H$_2$), 2.01–2.15 (4H, m, C4'—H$_2$, C16'—H$_2$), 2.79–2.87 (6H, m, C7'—H$_2$, C10'—H$_2$, C13'—H$_2$), 3.52 (2H, t, j6.6 Hz, C1'—H$_2$), 3.94 (2H, s, C2—H$_2$), 5.32–5.45 (8H, m, C5'—H, C6'—H, C8'—H, C9'—H, C11'—H, C12'—H, C14'—H, C15'—H);

$^{13}$C n.m.r. (50 mhz, CDCL$_3$) δ 169.82s, 130.48d, 129.97d, 128.55d, 128.42d, 128.08d, 128.02d, 127.96d, 127.59d, 81.402, 71.63t, 68.83t, 31.585, 29.295, 29.075, 28.14q, 27.23t, 27.01t, 25.66t, 22.57t, 14.09g.

t-Butyl Z, Z, Z-(6, 9, 12-octadecatrienyloxy) acetate (3b) [t-Bu β-oxa 21:3(n-6)]

$^1$H n.m.r. (200 Mhz, CDCl$_3$) δ 0.89 (3H, t, J 6.7 Hz, C18'—H$_3$, 1.25–1.45 (10H, m, C3'—H$_2$, C4'—H$_2$, C15'—H$_2$, C16'—H$_2$, C17'—H$_2$), 1.48 (9H, s, C(CH$_3$)$_3$), 1.56–1.68 (2H, m, C2'—H$_2$), 2.01–2.13 (4H, m, C5'—H$_2$, C14'—H$_2$), 2.77–2.84 (4H, m, C8'—H$_2$, C11'—H$_2$), 3.51 (2H, t, J6.6 Hz, C1'—H$_2$), 3.94 (2H, s, C2—H$_2$), 5.27–5.48 (6H, m, C6'—H, C7'—H, C9'—H, C10'—H, C12'—H, C13'—H);

$^{13}$C n.m.r. (50 mhz, CDCL$_3$) δ 169.82s, 130.41d, 130.10d, 128.33d, 128.21d, 127.87d, 127.64d, 81.39s, 71.72t, 68.82t, 31.52t, 29.57t, 29.49t, 28.12q, 27.18t, 25.74t, 25.63t, 22.56t, 14.04q.

t-Butyl Z, Z, Z-(9, 12, 15-octadecatrienyloxy)acetate (3c) [t-Bu β-oxa 21:3(n-3)]

$^1$H n.m.r. (200 Mhz, CDCl$_3$) δ 0.98 (3H, t, J 7.5 Hz, C18'—H$_3$, 1.25–1.40 (10H, m, C3'—H$_2$, C4'—H$_2$, C5'—H$_2$, C6'—H$_2$, C7'—H$_2$),1.48 (9H, s, C(CH$_3$)$_3$), 1.51–1.67 (2H, m, C2'—H$_2$), 2.01–2.15 (4H, m, C5'—H$_2$, C8'—H$_2$, C17'—H$_2$), 2.75–2.86 (4H, m, C11'—H$_2$, C14'—H$_2$), 3.50 (2H, t, J6.6 Hz, C1'—H$_2$), 3.95 (2H, s, C2—H$_2$),5.31–5.43 (6H, m, C6'—H, C9'—H, C10'—H, C12'—H, C13'—H, C15'—H, C16'—H);

$^{13}$C n.m.r. (50 mhz, CDCl$_3$) δ 169.84s, 131.94d, 130.35d, 128.27d, 127.66d, 127.13d, 81.36s, 71.83t, 68.82t, 29.64t, 29.45t, 29.25t, 28.12q, 27.24t, 26.04t, 25.62t, 25.53t, 20.53t, 14.25q.

t-Butyl Z, Z, Z, Z, Z, Z,-(4,7,10,13,16,19-docosahexaenyloxy)acetate (3d) [t-Bu B-oxa 25:6(n-3)

$^1$H n.m.r. (200 Mhz, CDCl$_3$) δ 0.98 (3H, t, J 7.5 Hz, C22'—H$_3$), 1.48 (9H, s, C(CH$_3$)$_3$), 1.58–1.76 (2H, m, C2'—H$_2$), 2.00–2.21 (4H, m, C3'—H$_2$, C21'—H$_2$), 2.79–2.87 (10H, m, C6'—H$_2$, C9'—H$_2$,, C12'—H$_2$), 3.52 (12H, m, C4'—H, C5'—H, C5'—H,C7'—H, C8'—H, C10'—H, C11'—H, C13'—H, C14'—H), C16'—H, C17'—H, C19'—H, C20'—H);

$^{13}$C n.m.r. (50 MHz, CDCL$_3$) δ 169.76s, 132.03d, 129.41d, 128.57d, 128.39d, 128.36d, 128.24d, 128.21s, 128.16d, 128.12t, 128.02d, 127.88d, 127.02d, 81.40s, 71.08t, 68.83t, 29.53t, 28.12q, 25.63t, 25.59t, 25.54t, 23.72t, 20.55t, 14.25q.

t-Butyl Z, Z, Z, Z,-(6, 9, 12, 15-octadecatetraenyloxy acetate (3e) [6/Bu β-oxa 21:4(n-3)

$^1$H n.m.r. (200 Mhz, CDCl$_3$) δ 0.98 (3H, t, J 7.5 Hz, C18'—H$_3$), 1.21–1.52 (4H, s, C3'H$_2$), 1.58–1.76 (2H, m, C2'—H$_2$), 1.48 (9H, s, C(CH$_3$) 3) 1.53–1.66 (2H, m, C2'—H$_2$,), 2.01–2.15 (4H, m, C5'—H$_2$, C17'—H$_2$),2.77–2.87 (6H, m C8'—H$_2$, C11'—H$_2$, C14'—H$_2$), 2.51 (3H, t, J6.6 Hz, C1'-h$_2$), 3.95 (2H, s, C2—H2), 5.28–5.47 (8H, m C6'—H, C7'H, C9'—H, C10'—H, C12'—H, C13'—H, C15'—H, C16'—H);

$^{13}$C/n.m.r. (50 MHz, CDCl$_3$) δ 169.82s, 132.00d, 130.15d, 128.49d, 128.42d, 128.old, 127.96d, 127.78s, 127.05d, 81.39s, 71.72t, 68.81d, 29.57t, 29.49t, 28.12q. 27.18t, 25.74t, 25.63q, 25.54t, 20.55t, 14.25q.

Z, Z, Z, Z (5, 8, 11, 14-Eicosatetraenyloxy) acetic acid (4a) [β-oxa 23:4(n-3)]

$^1$H n.m.r. (200 Mhz, CDCl$_3$) δ 0.89 (3H, t, J 6.6 Hz, C20'—H$_3$), 1.25–1.490 (8H, m, C3'—H$_{2, C17}$—H$_2$, C18'—H$_2$, C19'—H$_2$), 1.57–1.74 (2H, m, C2'—H$_2$), 2.00–2.14 (4H, m, C4'—H$_2$, C16'—H$_2$), 2.78–2.85 (6H, m, C7'—H$_2$, J6.0 HzM C1'—H$_2$) 4.08 (2H, s C2—H$_2$), 5.29–5.46 (8H, m, C5'—H, C6'—H, C8'—H, C9'—H, C11'—H, C12'—H, C14'—H, C15'—H));

$^{13}$C n.m.r. (50 MHz, CDCl$_3$) δ 173.37s, 130.47d, 129.64d, 128.55d, 128.24d, 128.13d, 128.02d, 127.86s, 127.152d, 71.81t, 31.49t, 29.49t, 29.21t, 27.20t, 26.88t, 26.03t, 25.63t, 25.63t, 22.54t, 14.02q.

Z, Z, Z (6, 9, 12-Octadecatrienyloxy) acetic acid (4b)
[β-oxa 21:3(n-6)]

$^1$H n.m.r. (200 Mhz, CDCl$_3$) δ 0.89 (3H, t, J 6.8 Hz, C18'—H3), 1.23–1.43 (10H, m, C3'—H2, C4'—H2, C15'—H2, C16'—H2, C17'—H2)), 1.51–1.71 (2H, m, C2'—H2), 2.00–2.10 (4H, m, C5'—H2, C14'—H2), 2.75–2.86 (4H, m, C8'—H2, C11'—H2), 3.60 (2H, t, J 6.6 Hz, C1'—H2) 4.17 (2H, s, C2—H2), 5.26–5.47 (6H, m, C6'—H, C7'—H, C9'—H, C10'—H, C12'—H, C13'—H)

$^{13}$C n.m.r. (50 MHz, CDCl$_3$) δ171.74s, 130.45d, 129.84d, 128.40d, 128.20d, 128.10d, 127.59d, 71.13d, 31.51d, 29.36d, 29.31d, 27.20d, 27.10d, 25.62d, 22.57d, 22.55d, 14.04q.

Z, Z, Z (9, 12, 15-Octadecatrienyloxy) acetic acid (4c)
[β-oxa 21:3(n-3)]

$^1$H n.m.r. (200 MHz, CDCl$_3$) δ 0.97 (3H, t, J 7.5 Hz. C18'—H$_3$), 1.25–1.43 (10H, m, C3'—H$_2$, C4'—H$_2$,C5'—H$_2$, C6'—H$_2$, C7'—H$_2$), 1.51–1.63 (2H, m, C2'—H$_2$), 2.01–2.15 (4H, m, C8'—H$_2$, C17'—H$_2$), 2.75–2.86 (4H, m, C11'—H$_2$, C14'—H$_2$), 3.55 (2H, t, J 6.5 Hz, C1'—H$_2$), 4.12 (2H, s, C2'—H$_2$), 5.28–5.46 (6H, m, C9'—H, C10'—H, C12'—H, C13'—H, C15'—H, C16'—H)

$^{13}$C n.m.r. (50 mhz, CDCL$_3$) δ 174.73s, 131.93d, 130.29d, 128.25d, 127.68d, 127.11d, 72.16t, 29.60t, 29.41t, 29.20t, 27.21t, 25.88t, 25.60t, 25.52t, 20.53t, 14.24q.

Z, Z, Z, Z, Z, Z—(4, 7, 10, 13, 16, 19-Docosahexaenyloxy) acetic acid (4d)
[β-oxa 25:6(n-3)]

$^1$H n.m.r. (200 MHz, CDCl$_3$) δ 0.97 (3H, t, J 7.5 Hz, C22'—H$_3$), 1.65–1.78 (2H, m, C2'—H$_2$), 2.01–2.21 (4H, m, C3'—H$_2$, C21'—H$_2$, C21'—H$_2$), 2.75–2.92 (10H, m, C6'—H$_2$, C9'—H$_2$, C12'—H$_2$, C15'—H$_2$, C18'—H$_2$), 3.57 (2H, t, J 6.41 Hz, C1'—H$_2$), 4.12 (2H, s, C2'—H$_2$,), 5.28–5.46(12H, m, C4'—H, C5'—H, C7'—H, C8'—H, C10'—H, C11'—H, C13'—H, C14'—H, C16'—H, C17'—H, C19'—H, C20'—H), 10.22 (1H, br, CO$_2$H)

$^{13}$C n.m.r. (50 MHz, CDCl$_3$) δ 172.99s, 132.04d, 129.98d, 128.75d, 128.59d, 128.49d, 128.38d, 128.28d, 128.22d, 128.17d, 128.08d, 127.86d, 127.01d, 71.48t, 29.26t, 25.64t, 25.59t, 25.54t, 23.55t, 14.25q.

Z, Z, Z—(6, 9, 12, 15-Octadecatetraenyloxy) acetic acid (4e)
[β-oxa 21:4(n-3)]

$^1$H n.m.r. (200 Mhz, CDCl$_3$) δ 0.97 (3H, t, J 7.5 Hz, C18'—H.), 1.33–1.40 (4H, m, C3'—H$_2$, C4'—H$_2$), 1.54–1.68 (2H, m, C2'—H$_2$), 2.00–2.15 (4H, m, C5'—H$_2$, C17'—H$_2$), 2.77–2.87 (6H, m, C8'—H$_2$, C11'—H$_2$, C14'—H$_2$), 3.56 (3H, t, J 6.6 Hz, C1'—H$_2$), 4.11 (2H, s, C2—H2), 5.24–5.45 (8H, m, C6'—H, C7'—H, C9'—H, C10'—H, C12'—H, C13'—H, C15'—H, C16'—H);

$^{13}$C n.m.r. (50 MHz, CDCl$_3$) δ 172.05s, 132.03d, 139.92d, 128.53d, 128.35d, 128.08d, 128.01d, 127.94d, 127.04d, 71.10t, 29.34t, 27.10t, 25.64t, 25.55t, 20.55t, 14.25q.

Synthesis of β and γ Thia fatty acids.

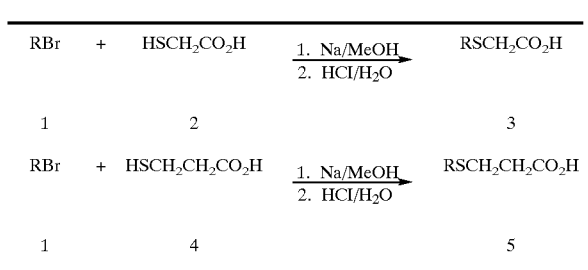

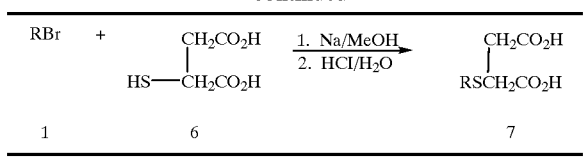

a: R=CH$_3$(CH$_2$)$_4$(CH$^{cis}$=CHCH$_2$)$_4$(CH$_2$)$_3$—
b: R=CH$_3$(CH$_2$)$_4$(CH$^{cis}$=CHCH$_2$)$_3$(CH$_2$)$_4$—
c: R=CH$_3$CH$_2$(CH$^{cis}$=CHCH$_2$)$_3$(CH$_2$)$_7$—
d: R=CH$_3$CH$_2$(CH$^{cis}$=CHCH$_2$)$_6$(CH$_2$)$_2$—

Reagents

Fatty bromides (1a–1d)—Synthesizes from the corresponding fatty alchohols by treatment with triphenylphosphine and carbon tetrabromide in dichloromethane.

Arachidonyl alchohol—Nu Chek Prep.
Gamma linolenyl alchohol—Nu Chek Prep
Linolenyl alchohol—Nu Check Preo
Docosaliexaenyl alchohol—Nu Chek Prep
Mercaptoacetic acid—Aldrich Chemical Company
Mercaptoproprionic acid—Aldrich Chemical Company
All solvents were distlilled prior to use.
Column chromatographies were performed under positive nitrogen pressure on Merck Silica Gel 60 (230–400mesh), Art. 9385.

Procedure

Alkylthioacetic acids 3a–d

Sodium (3 mol equivalents) was dissolved in methanol in a two-neck round-bottomed flask under dry nitrogen and to this stirred solution was added mercaptoacetic acid (1.2 mol equivalents). After the initial white precipitate had dissolved, a solution of the relevant bromide (1 mol equivalent) in diethyl ether was added vie syringe and the mixture was stirred at room temperature under nitrogen for 16 hr. The crude reaction mixture was poured into an equal volume of hydrochloric acid (10% v/v) and extracted with diethyl ether. The resulting extract was concentrated under a stream of dry nitrogen and the residue was purified by flash chromatography on silica, eluting with hexane/diethyl ether/acetic acid (40:60:2) to afford the relevant alkylthioacetic acid 3 as an oil.

Alkylthioprionic acids 5a–c

The alkylthioproprionic acids 5a–c were synthesized by alkaline condensation of the respective fatty bromides 1a–c with mercaptoproprionic acid 4. in an analogous manner to that described above for the alkylthioacetic acids 3a–d.

Z,Z,Z,Z-(5,8,11,14-Eicosatetraenylthio)succinic Acid 7a (5,8,11,14-Eicosatetraenylthio)succinic acid &a was synthesized by condensation of the fatty bromide 1a (1 mol equivalent) with mercaptosuccinic acid 6 (1.2 mol equivalents), in the presence of sodium (4.5 mol eqivalents) in an analogous manner to that described above for the alkylthioacetic acids 3a–d.

Z,Z,Z,Z-(5,8,11,14-Eicosatetraenylthio) acetic acid (3a)
[β-thia 23:4(n-6)]

$^1$H n.m.r. (200 Mhz, CDCl$_3$) δ 0.89 (3H, t, J6.7 Hz, C20'—H3), 1.21–1.54 (8H, m, C3'—H$_2$, C17'—H$_2$.C18'—H$_2$, C19'—H$_2$), 1.57–1.72 (2H, m, C2'—H$_2$), 2.01–2.14 (4H, m, C4'—H$_2$, C16'—H$_2$), 2.67 (2H, t, J 7.2 Hz, C1'—H$_2$)), 2.73–2.88 (6H, m, C7'—H$_2$C10'—H$_2$, C13'—H$_2$), 3.25 (2H. s, C2—H$_2$), 5.27–5.47 (8H, m, C5'—H, C6'—H, C8'—H, C9'—H, C11'—H, C12'—H, C154'—H, C15'—H);

$^{13}$C n.m.r. (50 MHz, CDCl$_3$) δ 175.69s, 130.49d, 129.54d, 128.56d, 128.27d, 128.15d, 127.89d, 127.55d, 33.45t, 32.70t, 31.51t, 30.38t, 29.32t, 28.62t, 28.46t, 27.23t, 26.73t, 25.65t, 22.57t, 14.05q.

Z,Z,Z,Z-(6,9, 12-Octadecatrienythio)acetica acid (3b) [β-thia 21:3(n-6)]

$^1$H n.m.r. (200 Mhz, CDCl$_3$) δ 0.89 (3H, t, J 6.6 Hz, C18'—H$_3$), 1.23–1.48 (10H, m, C3'—H$_2$,C4'—H$_2$,C15'—H$_2$, C16'—H$_2$, C17'—H$_2$), 1.52–1.70 (2H, m, C2'—H$_2$), 1.89–2.15 (4H, m, C5'—H$_2$, C14'—H$_2$). 2.63 (2H, t, J 7.0 Hz, C1'—H$_2$)), 2.70–2.87 (4H., m C8'—H$_2$ C11'—H$_2$), 3.26 (2H, s, C2—H1$_2$), 5.29–5.47 (6H, m, C6'—H, C7'—H, C9'—H, C10'—H, C12'—H, C13'—H);

$^{13}$C n.m.r. (50 MHz, CDCl$_3$) δ 176.54s, 130.41d, 129.54d, 129.86d, 128.367d, 128.11d, 128.03d, 128.59d, 33.49t, 32.74t, 31.51t, 30.36t, 29.31t, 29.14t, 28.81t, 28.34t, 27.27t, 27.05t, 25.63t, 22.55t, 14.05q.

Z,Z,Z,Z-(9,12,15-Octadecatrienylthio)acetic acid (3c) [β-thia 21:3(n-3)]

$^1$H n.m.r. (200 Mhz, CDCl$_3$) δ 0.89 (3H, t, J6.7 Hz, C18'—H$_3$), 1.21–1.52 (10H, m, C3'—H$_2$, C47'—H$_2$,C5'—H$_2$, C6'—H$_2$, C7'—H$_2$), 1.54–1.72 (2H, m, C2'—H$_2$), 2.01–2.15 (4H, m, C8'—H$_2$, C17'—H$_2$), 2.67 (2H, t, J 7.2 Hz, C1'—H$_2$)), 2.73–2.87 (4H, m, C11'—H$_2$, C14'—H$_2$), 3.25 (2H, s, C2—H$_2$), 5.27–5.48 (6H, m, C9'—H, C10'—H, C12'—H, C13'—H, C15'—H, C16'—H);

$^{13}$C n.m.r. (50 MHz, CDCl$_3$) δ 176.21s, 131.94d, 130.29d, 128.26d, 127.69d, 127.11d, 33.49t, 32.82t, 30.39t, 29.60f, 29.36t, 29.20t, 29.12t, 28.89t, 28.70t, 27.21t, 25.61t, 25.52t, 20.53t, 14.25q.

Z,Z,Z,Z-(9,12,15-Octadecatrienylthio)acetic acid (3d) [β-thia 25:6(n-3)]

$^1$H n.m.r. (200 Mhz, CDCl$_3$) δ 0.99 (3H, t, J 7.5 Hz, C22'—H$_3$), 1.62–1.77 (2H, m, C2'—H$_2$,), 2.02–2.24 (4H, m, C3'—H$_2$, C21'—H$_2$), 2.68 (2H, t, J 7.4 Hz C1'—H$_2$), 2.83–2.85 (10H, t, , C6'—H$_2$, C9'—H$_2$, C12'—H$_2$, C15'—H$_2$, C18'—H$_2$), 3.26 (2H, s, C2'—H$_2$), 5.29–5.47 (12H, m, C4'—H$_2$, C5'—H, C7'—H, C8'—H, C10'—H. C11'—H, C13'—H, C14'—H, C16'—H, C17'—H, C19'—H, C20'—H);

13C n.m.r. (50 MHz, CDCl$_3$) δ 176.37s, 132.01d, 128.94d, 128.68d, 128.55d, 128.24d, 128.18d, 128.12d, 128.07d, 127.85d, 126.99d, 33.41t, 32.21t, 28.67t, 26.12t, 25.64t, 25.22t, 25.22t, 20.53t, 14.24q.

Z,Z,Z,Z-(5,8,11,14-Eicosatetraenylthio) propionic acid (5a) [γ-thia 24:4(n-6)]

$^1$H n.m.r. (300 Mhz, CDCl$_3$) δ 0.89 (3H, t, J 6.8 Hz, C20'—H$_3$), 1.26–1.38 (6H, m, C17'—H$_2$, C18'—H$_2$, C19'—H$_2$), 1.41–1.51 (2H, m, C3'—H$_2$), 1.56–1.66 (2H, m, C2'—H$_2$), 2.02–2.12 (4H, m, C4'—H$_2$, C16'—H$_2$), 2.54 (42H, t, J 7.3 Hz, C3'—H$_2$), 2.78 (2H, t, J 6.6 Hz, C2—H$_2$), 2.78–2.86 (6H, m, C7'—H$_2$, C10'—H$_2$, C13'—H$_2$), 5.29–5.44 (8H, M, C5'—H, C6'—H, C8'—H, C9'—H, C11'—H, C12'—H, C14'—H, C15'—H);

$^{13}$C n.m.r. (50 MHz, CDCl$^3$) δ 178.22s, 130.37d, 129.58d, 128.46d, 128.19d, 129.10d, 128.03t, 127.81t, 127.48t, 34.68t, 32.046t, 31.44t, 29.25t, 29.01t, 28.67t, 27.15t, 26.70t, 26.54t, 25.57t, 22.50t, 13.98q.

Z,Z,Z,Z-(6,9,12-Octadecatrienylthio)propionic acid (5b) [γ-thia 22:3(n-6)]

$^1$H n.m.r. (200 Mhz, CDCl$_3$) δ 0.89 (3H, f, J 6.8 Hz, C18'—H$_3$), 1.25–1.42 (10H, m, C3'—H$_2$, C4'—H$_2$, C H$_2$, C16'—H$_2$, C17'—H$_2$), 1.53–1.65 (2H, m, C2'—H$_2$), 2.01–2.10 (4H, m, C5'—H$_2$, C14'—H$_2$), 2.53 (2H, t, J 7.3 Hz, C1'—H$_2$)), 2.66 (2H, t, J 6.8 Hz, C3'—H$_2$), 2.78 (2H, t, J 6.8 Hz C2—H1$_2$), 2.74–2.83 (4H, m, C8'—H, C11'—H) 5.26–5.47 (6H, m, C6'—H, C7'—H, C9'—H, C10'—H, C12'—H, C13'—H);

$^{13}$C n.m.r. (50 MHz, CDCl$_3$) 6178.14s, 130.38d, 129.90d, 128.33d, 128.10d, 127.97d, 127.58D, 34.69t, 32.13t, 31.49t, 29.41t, 29.29t, 29.18t, 28.46t, 27.19t, 27.06t, 26.58t, 25.61t, 14.03q.

Z,Z,Z,Z-(9,12,15-Octadecatrienylthio)proponionic acid (5c) [γ-thia 22:3(n-3)]

$^1$H n.m.r. (200 Mhz, CDCl$_3$) δ 0.98 (3H, t, J 7.5 Hz, C18'—H$_3$), 1.26–1.35 (10H, m, C3'—H$_2$, C4'—H$_2$,C5'—H$_2$, C6'—H$_2$, C7'—H$_2$), 1.51–1.65 (2H, m, C2'—H$_2$), 1.98–2.15 (4H, m, C8'—H2, C17'—H$_2$), 2.53 (2H, t, J 7.3 Hz, C1'—H$_2$), 2.66 (2H, t, J 6.7 Hz, C3'—H$_2$), 2.78 (2H, t, J 7.3 Hz, C1—H$_2$), 2.66 (2H, t, J 6.7 Hz, C3'—H$_2$), 2.78 (2H, t, J 6.7 Hz, C2'—H$_2$), 2.75–2.84 (4H, m, C11'—H$_2$, C14'—H$_2$) 5.27–5.46 (6H, m, C9'—H, C1o'—H, C12'—H, C13'—H, C15'—H, C16'—H);

$^{13}$C n.m.r. (50 MHz, CDCl$_3$) δ 178.03s, 131.92d, 130.28d, 128.24d, 127.66d, 127.10d, 34.67t, 32.19t, 29.58t, 29.50t, 29.37t, 29.20t, 29.16t, 28.81t, 27.19t, 26.59t, 25.59t, 25.50t, 20.52t, 14.245q.

Z,Z,Z,Z-(5,8,11,14-Octadecatrienylthio)succinic acid (7a) [α-carboxymethyl-β-thia 23:4(n-6)]

$^1$H n.m.r. (300 MHz, CDCl$_3$) δ 0.89 (3H, t, J 6.8 Hz, C20'—H$_3$), 1.23–1.53 (8H, m, C3'—H$_2$, C17'—H$_2$, C18'—H$_2$, C19'—H$_2$), 1.56–1.70 (2H, m, C2'—H$_2$), 2.03–2.13 (4H, m, C4'—H$_2$, C16'—H$_2$), 2.65–2.86 (9H, m, C7'—H$_2$, C10I-H$_2$, C13'—H$_2$, C1'—H$_2$, CHHCO$_2$H), 3.01 (1H, dd, J 12.1, 17.6 Hz, CHHCO$_2$H), 3.64 (1H, dd, J 4.0, 12.1 Hz, C2—H), 5.32–5.43 (8H, m, C5'—H, C6'—H, C8'—H, C9'—H, C11'—H, C12'—H, C14'—H, C15'—H);

Synthesis of Hydroxy and Hydoperoxy Derivatives.

Figure 1M:
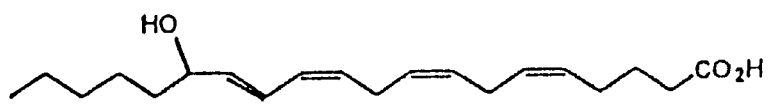
FIG. 1*m* shows 15-Hydroperoxy-5Z, 8Z, 11ZE, 13E Eicosatetraenoic acid.
Figure 1N:
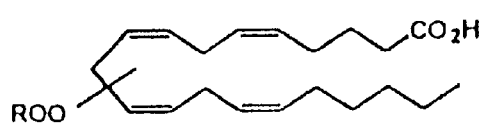
FIG. 1*n* to FIG. 1*z* show a range of substituted PUFAs in which Y is hydroxy, hydroperoxy or peroxy.
Figure 1O:
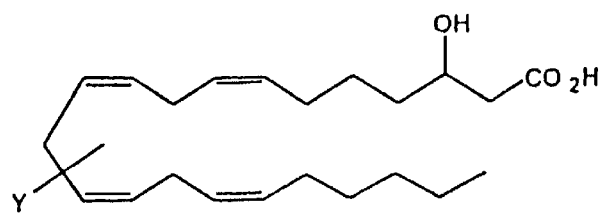
Figure 1P:
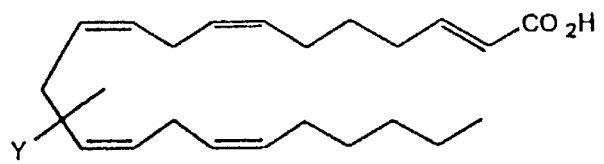
Figure 1Q:
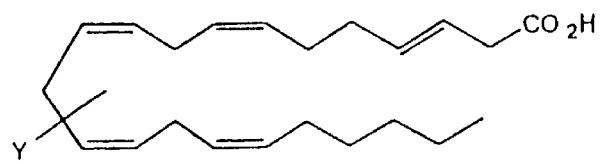
Figure 1R:
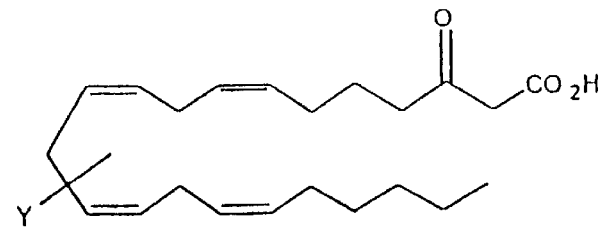
Figure 1S:
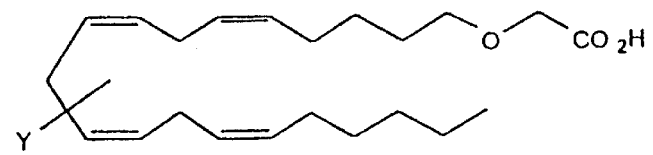
Figure 1T:
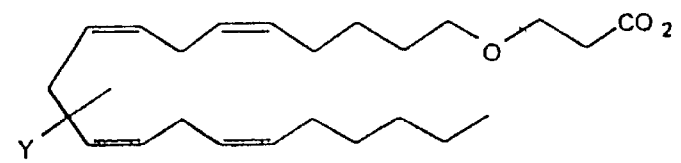
Figure 1U:
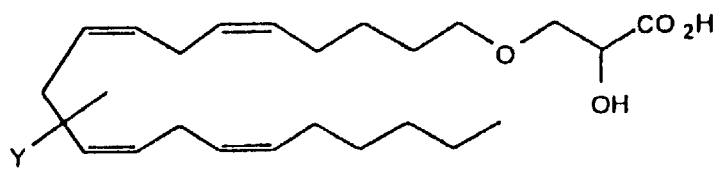
Figure 1V:
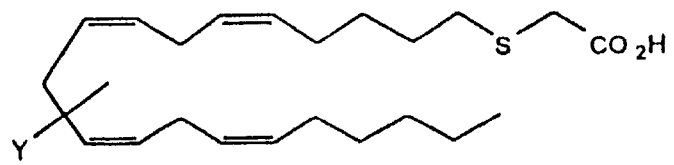
Figure 1W:
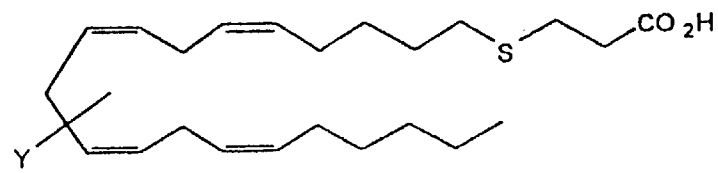
Figure 1X:
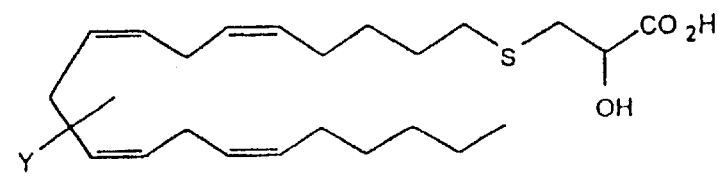

The hydroperoxide derivatives of arachidonic acid (FIGS. 1b–1g) are obtained separately from enzymlie-catalysed reactions of 1, or as a mixture by autoxidation of 1a. The components of the autoxidationi mixture FIGS. 1b–1g, which vary in ratio depending on the reaction conditions, can be separated by high performance liquid chromatography on silica. Reduction of the hydroperoxides FIGS. 1b–1g, either separately or as a mixture affords the corresponding alchohols FIGS. 1h–1m. These can be converted to the corresponding peroxides FIG. 1n (R-alkyl or aryl). having the same substitiution pattern as the hydroperoxides FIGS. 1b–1g and alcohols FIGS. 1n–1m, by treating with a variety of reagents including the corresponding alkyl or aryl hypohalites (ROX). Mixtures of either the alchols FIGS. 1n–1m or the peroxides FIG. 1n can also be separated by high performance liquid chromatography.

Figure 1Y:
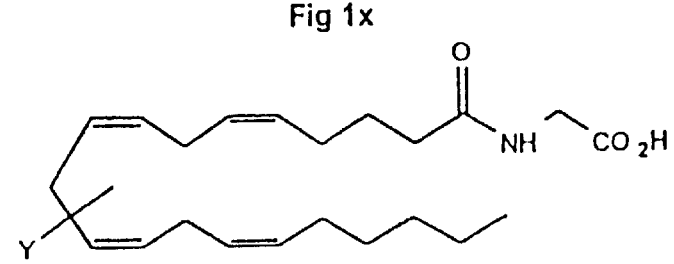
Figure 1Z:
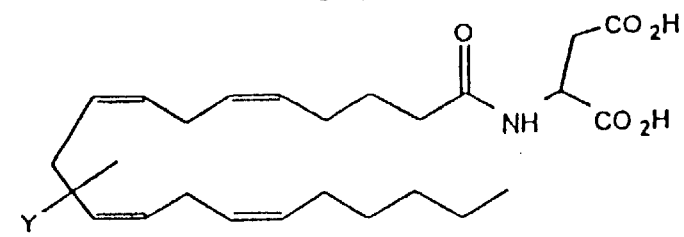
Figure 2A:
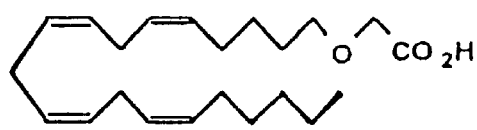
FIG. 2*a* shows β-oxa 23:4 (n-6)
Figure 2B:
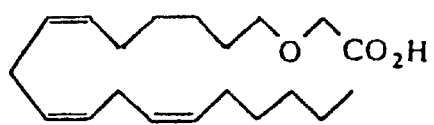
FIG. 2*b* shows β-oxa 21:3 (n-6)
Figure 2C:
FIG. 2*c* shows β-oxa 23:4 (n-3)
Figure 2D:
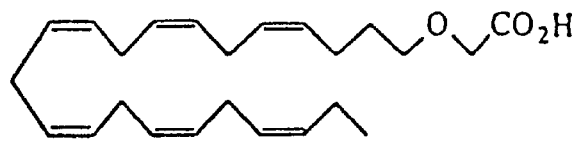
FIG. 2*d* shows β-oxa 25:6 (n-3)
Figure 2E:
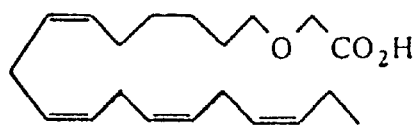
FIG. 2*e* shows β-oxa 21:4 (n-3)
Figure 2F:
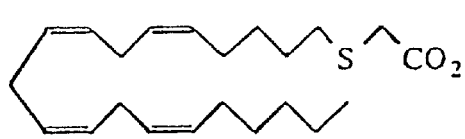
FIG. 2*f* shows β-thia 23:4 (n-6)
Figure 2G:
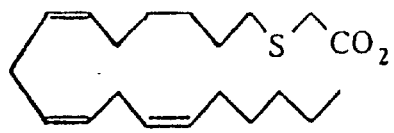
FIG. 2*g* shows β-thia 21:3 (n-6)
Figure 2H:
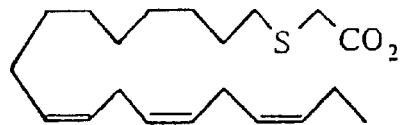
FIG. 2*h* shows β-thia 21:3 (n-3)
Figure 2I:
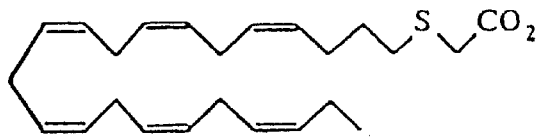
FIG. 2*i* shows β-thia 25:6 (n-3)
Figure 2J:
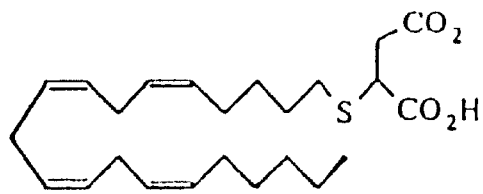
FIG. 2*j* shows α-carboxymethyl-β-thia 23:4 (n-6)
Figure 2K:
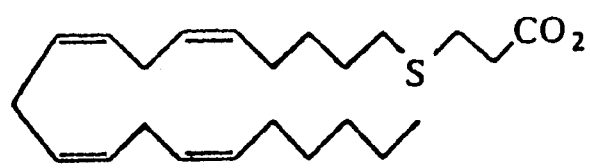
FIG. 2*k* shows γ-thia 24:4 (n-6)
Figure 2L:
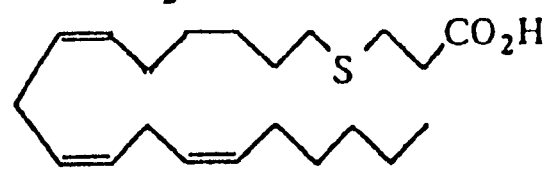
FIG. 2*l* shows γ-thia 22:3 (n-6)
Figures 2M, 2N:
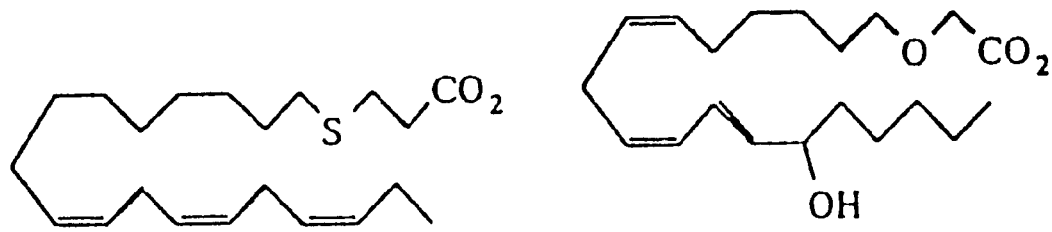
FIG. 2*m* shows γ-thia 22:3 (n-3)
FIG. 2*n* shows 16-OH-β-oxa 21:3 (n-6)
Figure 2O:
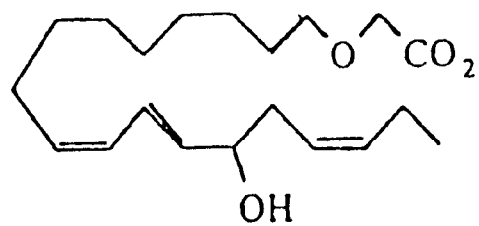
FIG. 2*o* shows 16-OH β-oxa 23:4 (n-6)
Figure 5:
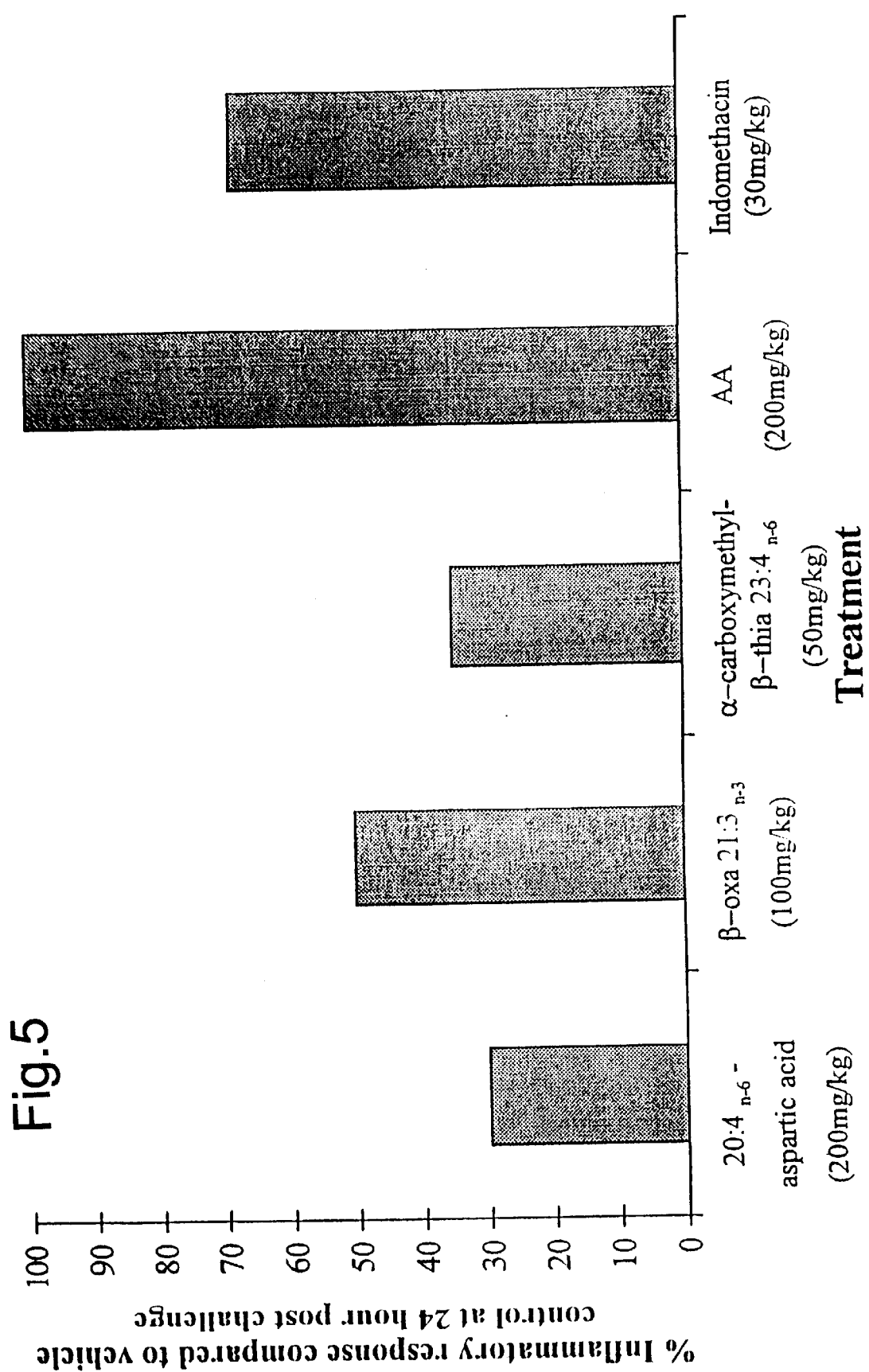
FIG. 5 shows the effect of novel PUFA 20:4—aspartic acid, β oxa 21:3n-3 and a carboxymethyl β thia 23:4n-6 on the delayed type hypersensitivity response induced by sheep red blood cells.
Figure 6:
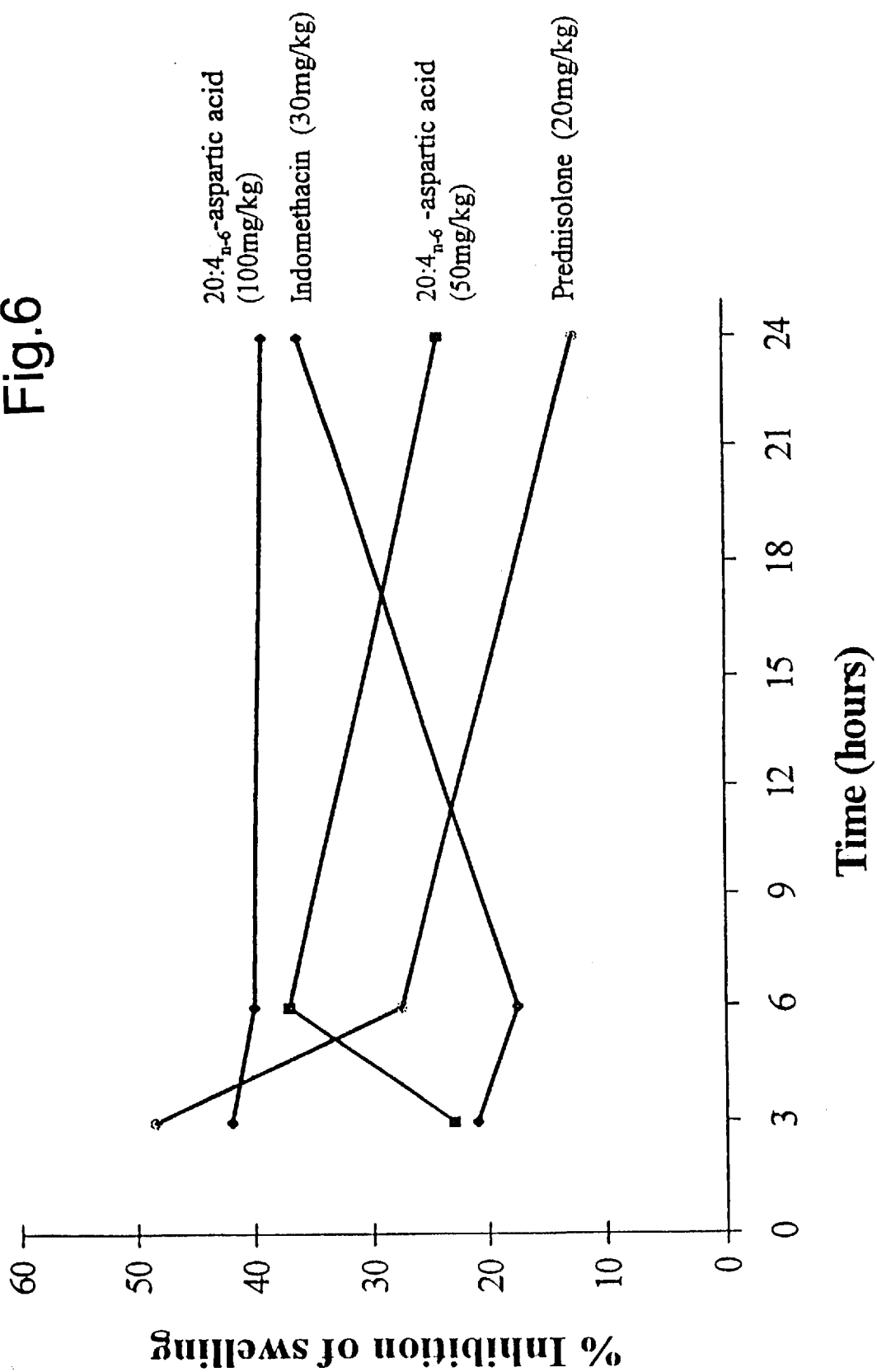
FIG. 6 shows the effect of 20:4n-6—aspartic acid on carrageenan-induced paw oedema.
Figure 7:
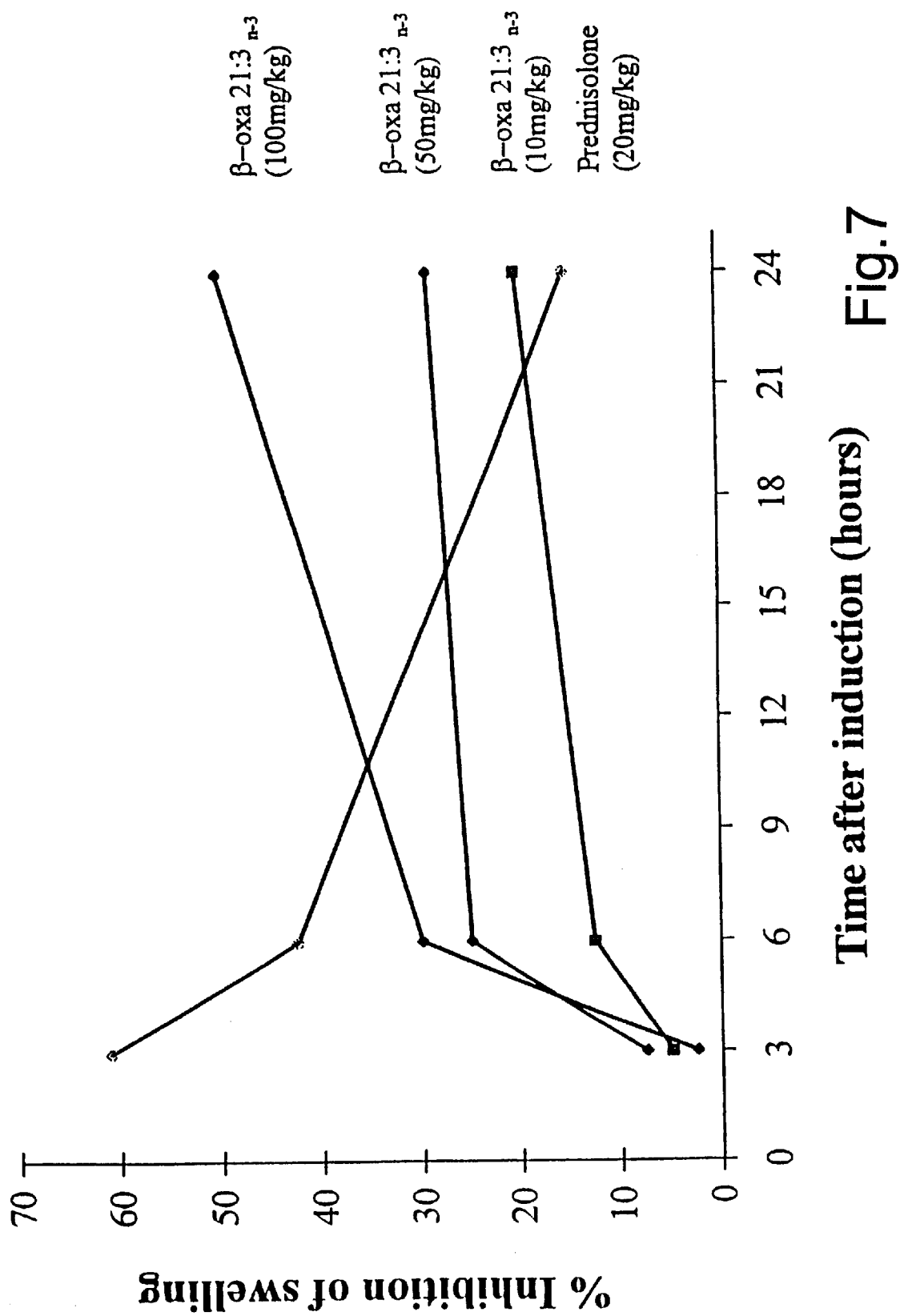
FIG. 7 shows the effect of β oxa 21:3 n-3 on carrageenan-induced paw oedema.

In a similar fashion other naturally occuring unsaturated fatty acids (eg 22:6 (n-3)), and modified fatty acids such as FIGS. 1o–1x (Y=H) and related compounds prepared by elaboration of acids other that arachidonic acid can be used to prepare hydroperoxy, hydroxy and peroxy derivatives FIGS. 1o–1x (Y=OOH, OH, OOR), analogous to 2–14, where the substitution pattern is determined by the allyic oxidation. The acids FIG. 1o and FIG. 1p (Y=H) can be prepared by aldol condensation of the corresponding aldehyde of FIG. 1a and FIG. 1p can also be prepared via a Wittig reaction of the same aldehyde or the corresponding halide, while the acid FIG. 1q can be prepared via a Wittig reaction of the corresponding C19 aldehyde or halide. The acid 18 can be prepared by aldol condensation of a corresponding ester of FIG. 1a, while FIGS. 1s–1x are obtained by ether or thioether synthesis, through nucleophilic substitution or metal catalysed coupling reactions, and the thioethers FIGS. 1v–1x can be oxidised to the corresponding sulphoxides and sulphones. The amino acid derivatives FIG. 1y and FIG. 1z can be obtained by coupling the corresponding fatty acid FIG. 1a and glycine and aspartic acid respectively.

Synthesis of Hydroxy β-Oxa Fatty Acids

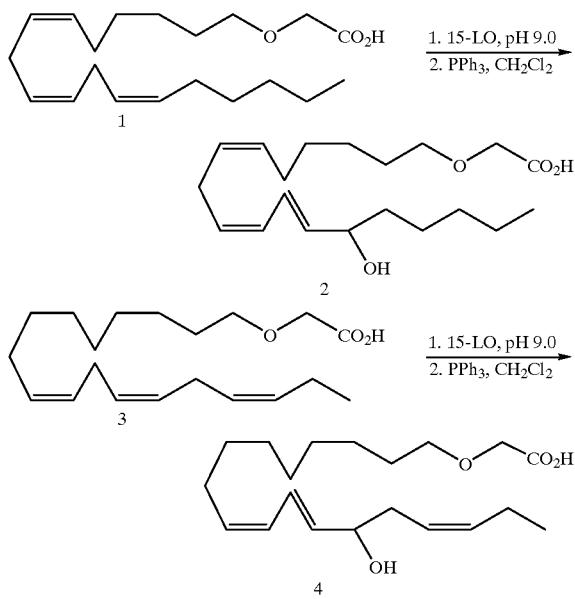

Reagents

β-oxa Fatty Acids (1,3)—synthesized from the corresponding fatty alcohols by rhodium acetate catalysed coupling with diazoacetate esters.

Triphenyilphosphine—Aldrich Chemical Company.
Potassium Dihfydrogen Orthopliosphate—Ajax Chemicals.
Soybean 15-Lipoxygenase—Aldrich Chemical Company.
All solvents were distilled prior to use.
Preparative layer chromatographies were performed on Merck Silica Gel 60
$PF_{254}$ containing gypsum; Art 7749.

Procedure

Hydroxy β-oxa Fatty Acids 2 and 4

The relevant fatty acid, 1 and 3, (ca. 50 mg) was dissolved in phosphate buffer (0.1 M, pH=9.0, ca. 45 ml) at 30° C. Soybean 15-lipoxygenase (ca. 8 mg) in phosphate buffer (ca. 5 ml) was added and oxygen was bubbled through the stirred solution for 10 min. Triphenylphosphine (ca. 50 mg) was added in dichloromethane (ca 50 ml) followed by hydrochloric acid (0.2 M, ca 20 ml) and the solution was stirred at 0° C. for 20 min. The crude reaction mixture was extracted with dichloromethane and the resulting extract was concentrated under a stream of dry nitrogen. The residue was purified by preparative layer chromatography on silica, eluting with ethyl acetate/hexane/acetic acid (80:20:0.1), to afford the respective hydroxy β-oxa fatty acid, 2 or 4. as an oil Z, Z, E-(13-Hydroxy-6,9,1-octadecatienyloxy) acetic acid (2)

[13'-OH-β-oxa 21:3(n-6)]

$^1H$ n.m.r. (300 MHz, $CDCl_3$) δ 0.89 (3H, t, J 6.8 Hz, C18'—$H_3$), 1.25–1.45 (10H, m, C3'—$H_2$, C4'—$H_2$, C15'—$H_2$, C16'—$H_2$, C17'—$H_2$), 1.59 –1.73 (2H, m, C2'—$H_2$), 2.01–2.12 (4H, m, C5'—$H_2$, C14'—$H_2$), 2.81 (2H, t, J 5.8Hz, C8'—$H_2$), 3.52–3.60 (2H, m, C1'—$H_2$), 4.10 (2H, s, C2—$H_2$), 4.20 (1H, dt, J 6.0, 6.7 Hz, C13'—H) 5.29–5.45 (3H, m, C6'—H, C7'—H, C9'—H), 5.70 (1H, dd, J 6.7 15.2 Hz, C12'—H) 5.99 (1H, dd, J 10.9 Hz, Clo'—H) 6.55 (1H, dd, J 10.9, 15.2 Hz, C11'—H)

Z, E, Z-(13-Hydroxy-9, 11, 15-octadecatrienyloxy)acetic acid (4)

[13'-OH-β-oxa 21:3(n-6)]

$^1H$ n.m.r. (300 MHz, $CDCl_3$) δ 0.95 (3H, t, J 7.6 Hz, C18'—$H_3$), 1.17–1.40 (10H, m, C3'—$H_2$, C4'—$H_2$, C5'—$H_2$, C6'—$H_2$, C7'—$H_2$), 1.48–1.63 (2H, m, C2'—$H_2$), 1.99–2.12 (2H, m, C8'—$H_2$), 2.13–2.22 (2H, m, C14'—$H_2$) 2.28–2.37 (2H, m, C17'—$H_2$), 3.44–3.50 (2H, m, Cl'—$H_2$), 3.80–3.92 (2H, s, C2'—$H_2$), 4.14–4.20 (1H, dt, 16.4. 14.9 Hz, C13'—H), 5.30–5.60 (3H, m, C9'—H, C15'—H, C16'—H), 5.67 (1H, dd, J6.4, 14.9 Hz, C12'—H), 5.95 (1H, dd, J 11.1, 11.1 Hz, C10'—H), 6.49 (1H, dd, J 11.1, 14.9 Hz C11'—H)

Synthesis of Arachedonic Acid-Glycine-OH

Arachidonic acid (0.50 g) was dissolved in DMF (2.0 mL), HOSu (0.38 g om 0.5 mL DMF) and H-Gly-OtBu.HCl (0.55 g in 1.5 mL DMF) were added. The mixture was cooled in an ice bath. DCC (0.41 g in 0.5 mL DMF) was added. N-MM was added and the mixture was stirred for 30 minutes in ice bath and then stireeed at room temperature for 20 hours. The reaction did not go to completion and about 20–3-% arachidonic acid was not reacted. More DCC (0.16 g), HOSu (0.19 g), H-Gly-OtBu.HCl (0.20 g) and N-MM (0.24 g) were added and the mixture was stirred for 24 hours. DCU was filtered off and the product was isolated by preparative HPLC and lyophilised to yield a pale green oil (0.67 g, 98%). The oil of arachidonic-Gly-OtBu was redissolved in neat trifluoroacetic acid (40 mL) in ice bath and stirred for 30 min and then at rooin temperature for further 30 minutes. TFA was evaporated to yield arachidonic-Gly-OH as a muddy green oil (0.53 g). It was purified by PHLC and lyophilised to yield a light yellow gluey solid (0.23 g, 39%).

Purification

Preparative HPLC conditions:
buffer A:0.1% TFA/$H_2O$, buffer B: 0.1% TFA/10%$H_2O$/90%$CH_3CN$.

40 mL/min, 214 nm, C18 semiPrepPak

Stepwise increments of %B: 10—20—30—40—50—60—70—80—90—100%

Arachidonic acid eluted at 60% B, arachidonic-Gly-OH eluted at 75–80% B. arachidonic-Gly-OtBu eluted at 80–85% B.

1. HPLC buffer: 0.1% TFA/10% $H_2O$/90% $CH_3CN$ 2 mL/min, 214 nm, C18 NovaPak isocratic Retention times of components:

Arachidonic acid: Rt 4.14 min

Arachidonic-Gly-OH: Rt 2.78 min

Arachidonic-Gly-OtBu: Rt 5.23 min

2. $^{13}C$ n.m.r.

Arachidonic-Gly-OH

—(DMSO-d6): 14.1, C20, 22.1, 25.4, 26.4, 26.8, 28.9, 31.0, 34.7, 10 x $CH_2$; 40.7, Ga; 127.7, 127.85, 127, 93, 128.2, 128.3, 129.6, 130.1, 8 x CH; 171.5, C=O, G; 172.5, Cl.

3. FAB-MS m/z 362 (M+1)

4. Amino acid analysis

Gly present

Synthesis of Arachidonic-Aspartic Acid-OH

Arachidonic acid, HOSu and H-Asp(OtBu)-OtBu.HCl were dissolved together in DMF (3 mL). The mixture was cooled in an ice bath and DCC in DMF (0.7 mL) was added.

N-MM was added and the mixture was stirred for 20 hours. About 20% arachidonic acid retnained. More HOSu (0.19 g), H-Asp (OtBu)-OtBu.HCl (0.30 g), Dcc (0.16 g) and N-MM (0.24 g) were added and the mixture was stirred for further 20 hours. DCU was filtered off and the product was isolated by HPLC. The purified Ara-Asp (OtBu)-OtBu was concentrated to an oil and TFA (25 mL) was added. After an hour stirring, TFA was evaporated to yield a dark green oil. Arachidonic-Asp-OH was purified by HPLC. The pure fractions of Ara-Asp-OH were combined, concentrated and lyophilised (in tBu-OH) to yield brown oil (0.38 g, 55%).

Purification

HPLC purification:

buffer A: 0.1% TFA, buffer B: 0.1% TFA=+10% $H_2O$+90% $CH_3CN$ 40 m:/min, 214 nm, C18 SemiPrepPak Stepwise increments of % B: 10%—20—30—40—50—60—70—80—85— 100% B.

Arachidonic acid eluted at 70% B.

Arachidonic-Asp(OtBu)-OtBu eluted at 80% B.

Arachidonic-Asp-OH eluted at 60% B.

Analysis

1. HPLC buffer: 0.1% TFA+10% $H_2O$+90% $CH_2CN$ 2 mL/min, 214 nm, C18 NovaPak

Isocratic

Retention times:

Arachidonic acid: Rt 4.12 min

Arachidonic-Asp(OtBu)-OtBu: Rt 9.52 min

Arachidonic-Asp-OH: Rt 2.31 min

2. $^{13}C$ n.m.r.

Arachidonic=Asp-OH

—(DMSO-d6): 14.1, $CH_3$; 22.2, 24.6, 25.4, 26.3, 26.8, 26.9, 28.9, 31.1, 33.3, 10 x $CH_2$; 34.4, ??; 36.2, DO; 48.7, Da; 67.1, ??; 127.7, 127.88, 127.97, 128.181.128.23, 129.6, 130.1, 8 x CH; 171.6, D-; 172.1, C=O, Asp; 172.7, C=O, Arachidonic.

Arachidonic acid

—(DMSO-d6): 14.1, $CH_3$; 22.2, 24.6, 25.4, 26.3, 26.8, 26.9, 28.9, 31.1, 33.3,10 x $CH_2$; 127.7, 127.9, 128.0, 128.2, 128.3, 128.4, 129.3, 130.1, 8 x CH; 174.5, C=O.

3. FAB-MS and CI-MS m/z 420 (M+1)

4. Amino acid analysis

Asp present.

Synthesis of Eicosapentaenoic Acid-Glycine-OH

Eicosapentaenoic acid, H-Gly-OtBu.HCl and HOSu were dissolved together in DMF (4 mL). The mixture was cooled in ice bath and DCC (in 1 mL DMF) was added. N-methylmorpholine was added and the mixture stirred in ice bath for 20 minutes and then at room temperature for 20 hours. 36% of eicosapentaenoic acid remained unreacted. More H-Gly-OtBu-HCl (0.22 g), HOSu (0.15 g), DCC (0.16) g) and N-MM (0.27 g) were added and stirred for further 20 hours. Some eicosapentaenoic acid remained (about 30% by HPLC). The mixture was filtered and the crude product was purified by HPLC to yield Epe-Gly-OtBu as coloured oil (0.49 g, 71%). The oil was redissolved in cold trifluoroacetic acid (30 mL) and stirred fro an hour. TFA was evaporated to leave a black oil. The crude Epe-Gly-OH was purified by HPLC to yield 0.13 g (22%) brown oil).

Purification

HPLC purification:

buffer A: 0.1% TFA/$H_2O$ buffer B: 0.1% TFA+10% $H_2O$+90% $CH_3CN$ 40 mnL/min, 214 nm, C18 SemiPrepPak Increments of % B: 10—20—30—40—50—55—60—65—68—70% B.

Epe acid and Epe-Gly-OtBu eluted at 65–70%B. It was able to isolate some pure fractions of Epe-Gly-OH. Fractions containing the two compounds were combined and repurified.

Under the same conditions as above, Epe-Gly-OH eluted at 60% B.

Analysis

1. Analytical IIPLC

Buffer: 011% TFA+10% $H_2O$+90% $CH_3CN$ 2 mL/min, 214 nm, C18 Novapak isocratic Retention times of reaction components:

eicosapentaenoic acid: Rt 3.1 min

Epe-Gly-OtBu: Rt 3.9 min

Epe-Gly-OH: Rt 2.1 min

2. $^{13}C$ n.m.r.

(DMSO-d6): 14.3, $CH_3$; 20.2, 25.4, 34.8, $CH_2$; 40.7, Ga; 127.2, 127.9, 128.1, 128.2, 128.3, 129.7, 131.8, CH; 172.6, 172.5, C=O.

3. CI-MS m/z 360 (M+1).

Synthesis of Eicosapentaenoic Acid-Aspartic Acid-OH

Eicosapentaenoic acid, H-Asp(OtBu)-OtBu.HCl and HOSu were dissolved together in DMF (4 mL). The mixture was cooled in the ice bath and Dcc (in 1 mL DMF) was added. N-Methylmorpholine was added and the mixture was stirred in ice bath for 20 minutes and then at room temperature for 20 hours. About 23% Epe acid by HPLC remained. More H-Asp(OtBu)-OtBu.HCl (0.28 g), HOSu (0.11 g), DCC (0.12 g) and N-MM (0.20 g) were added and the mixture stirred for further 20 hours. About 17% Epe acid remained. The mixture was filtered and the crude Epe-Asp (OtBu)-was purified by HPLC and yielded 0.83 g (940/v) brown oil. Cold trifluoroacetic acid (30 mL) was added to the brown oil and the mixture stirred for an hour. TFA was evaporated to leave a dark brown oil which was redissolved in $CH_3CN$ (10 mL) and was purified by HPLC. The pure Epe-Asp-OH weighed 0.50 g (72%/o).

Purification

Buffer A: 0.1% TFA/H20

Buffer B: 0.1% TFA+10% $H_2O$+90% $CH_3CN$ 40 mL/min, 214 nm, C18 SemiPrepPak

Increments of %B: 10%—20—30—40—50—52—55—57—60—65—68—70%

Epe acid eluted at 65% B, Epe-Asp(OtBu)-OtBu eluted at 70% B, Epe-Asp-OH eluted at 55% B.

Analysis

1. Analytical HPLC

Buffer: 0.1% TFA+10% $H_2O$+90% $CH_3CN$ 2 mL/min, 214 nm, C18 NovaPak, isocratic Retention times:

Epe acid: Rt 3.1 min

Epe-Asp(OtBu)-OtBu: Rt 6.7 min

Epe-Asp-OH: Rt 1.8 min

2. $^{13}C$ n.m.r.

(DMSO-d6): 14.3, $CH_3$; 20.2, 25.3, 25.4, 26.4, 31.5, 34.8, 8 x $CH_2$; 36.3, DP; 48.7, Da; 127.2, 127.92, 127.97, 128.1, 128.2, 128.3, 129.7, 131.8, 10 x CH; 171.9, 172.1, 172.7, 3 x C=O.

3. CI-MS m/z 418 (M+1)

Synthesis of Docosahexaenoic Acid-Glycine-OH

H-Gly-OtBu.HCl and HOSu were dissolved together in DMF (2 mL). The mixture was cooled in ice bath and docosahexaenoic acid, DCC (in 0.4 mL DMF), and N-methylmorpholine were added. The mixture stirred in ice bath for 30 minutes and then at room temperature for 5 hours. 30% docosahexaenoic acid (Dhe acid) remained. More DCC (0.11 g) was added and the mixture stirred for further 20 hours. About 28% Dhe acid remained. The mixture was filtered and the crude product was purified by UPLC. The lyophilised Dhe-Gly-OtBu (light yellow oil) weighed 0.62 g (92%). Cold TFA (30 mL) was added to the oil and the mixture stirred for an hour. TFA was evaporated to leave a dark brown oil which was redissolved in $CH_3CN$ (10 mL) and was purified by HPLC. The purified Dhe-Gly-OH was lyophilised to leave a dark brown oil (0.27 g, 46%)/

Purification

HIPLC conditions:

Buffer A: 0.1% $TFA/H_2O$

Buffer B: 0.1% TFA+10% $H_2O$+90% $CH_3CN$ 40 mL/min, 214 nm, C18 SemiPrepPak manual increment of % B: 10%—20—30—40—50—55—60—65—70—73— 100% B.

Both Dhe acid and Dhe-Gly-OtBu eluted at 71–73% B. The acid eluted slightly earlier than Dhe-Gly-OtBu.

Dhe-Gly-OH eluted at 60% B.

Analysis

1. Analytical HPLC

Buffer: 0.1% TFA+10% $H_2O$+90% $CH_3CN$ 2 mL/min, 214 nm, C18 NovaPak

Retention times of reaction components:

Dhe acid: Rt 3.6 min

Dhe-Gly-OtBu: Rt 4.5 min

Dhe-Gly-OH: Rt 2.5 min

2. $^{13}C$ n.m.r.

(DMSO-d6): 14.3, $CH_3$; 20.2, 23.2, 25.3, 25.36, 25.42, 35.1, 8 x $CH_2$; 40.8, Ga; 127.1, 127.90. 127.98, 128.06, 128.1, 129.27, 128.3, 129.1, 131.8, 6 x CH; 171.5, 172.0, 2 x C=O.

3. CI-MS m/z 386 (M+1)

Synthesis of Docosahexaenoic Acid-Aspartic Acid-OH

H-Asp(OtBu)-OtBu.HCl and HOSu were dissolved together in DMF (2 mL). The mixture was cooled in ice bath and docosahexaenoic acid, DCC (in 0.4 mL DMF), and N-methylmorpholine were added. The mixture stirred in ice bath for 30 minutes and then at room temperature for 4 hours. 30% docosahexaenoic acid (Dhe acid) remained. More DCC (0.11 g) was added and the mixture stirred for further 20 hours. About 18% Dhe acid remained. The mixture was filtered and the crude product was purified by HPLC. The lyophilised Dhe-Asp(OtBu)-OtBu (light yellow oil) weighed 0.73 g (86%). Cold TFA (30 mL) was added to the oil and the mixture stirred for an hour. TFA was evaporated to leave a dark brown oil which was redissolved in $CH_3CN$ (5 mL) and was purified by HPLC. The purified Dhe-Gly-OH was lyophilised to leave a dark brown oil (0.33 g. 49%).

Purification

HPLC conditions:

Buffer A: 0.1% $TFA/H_2O$

Buffer B: 0.1% TFA+10% $H_2O$+90% $CH_3CN$ 40 mL/min, 214 nm, C18 SemiPrepPak manual increment of % B: 10%—20—30—40—50—55—60—65—68—70—73— 75% B.

Dhe acid eluted at 73% B. Deh-Asp(OtBu)-OtBu eluted at 73–75%B. Dhe-Asp-OH eluted at 58% B.

Analysis

1. Analytical HPLC

Buffer: 0.1% TFA+10%$H_2O$+90% $CH_3CN$ 2 mL/min, 214 nm, C18 NovaPak

Retention times of reaction components:

Dhe acid: Rt 3.6 min

Dhe-Asp (OtBu: Rt 8.2 min

Dhe-Asp-OH: Rt 2.0 min

2. $^{13}C$ n.m.r, (DMSO): 14.3, $CH_3$; 20.2,23.2, 25.3, 25.4, 25.4, 35.0, 8 x $CH_2$; 36.4, Dβ; 48.7, Da; 127.1, 127.9, 127.98,128.0, 128.1, 128.22, 128.28, 128.3, 129.0, 131.8, CH; 171.6, 171.8, 172.7, 3 x C=O.

3. CI-MS m/z 444 (M+1)

Synthesis of Linolenic Acid-Glycine-OH

Linolenic acid, HOSu and H-Gly-OtBu.HCl were dissolved together in DMF (3 mL), the mixture cooled in ice bath and DCC (ill 0.3 mL DMF) added. N-MM was added and the mixture stirred for 20 hours, after which time some unreacted linolenic acid remained. More DCC (0.10 g) was added and the mixture stirred for further 20 hours. DCU was filtered off and the product isolated by reverse phase HPLC. The purified product was concentrated to an oil and TFA (30 mL) was added. After an hour stirring, the TFA was evaporated to leave the product as a brown oil which was redissolved in $CH_3CN$ (6 mL) and was purified by HPLC. The pure fractions obtained were combined, concentrated and lyophilised (in t-butanol) to yield a brown oil (0.24 g, 40%).

Purification

HPLC purification

Buffer A: 0.1% $TFA/H_2O$

Buffer B: 0.1% TFA+10% $H_2O$+90% $CH_3CN$ 40 mL/min, 214 nm, C18 small prep column Lino-Gly-OH eluted at 65% B, linolenic acid eluted at 67% B, linolenvl-Gly-OtBu eluted also at 67% B but slightly later.

Analysis and Characterisation

1. Analytical HPLC

Buffer A: 0.1%, buffer B: 0.1% TFA/10%1120/90% $CH_3CN$ 2 mL/min, 214 nm, C18 NovaPak 100% B isocratic, retention times of ingredients:

linolenic acid: Rt 3.96 min linolenyl-Gly-OtBu: Rt 4.63 min linolenyl-Gly-OH: Rt 2.59 mil 2. $^{13}C$ n.m.r.

(DMSO-d6): 14.2, $CH_3$; 20.2, 25.26, 25.32, 26.8, 28.7, 28.8, 29.2, 35.2, $CH_2$; 40.7, Ga; 127.1, 127.7, 128.1, 130.1, 131.7, CH; 171.6, 172.7, C=O.

3. CI-MS m/z 336 (M+1)

Synthesis of Linolenic Acid-Aspartic Acid-OH

Linolenic acid, HOSu and H-Asp(OtBu)-OtBu.HCl were dissolved together in DMF (3 mL), the mixture cooled in ice bath and DCC (in 0.3 mL DMF) added. N-MM was added and the mixture stirred for 20 hours, after which time some unreacted linolenic acid remained. More DCC (0.10 g) was added and the mixture stirred for further 20 hours. DCU was filtered off and the product isolated by reverse phase HPLC. The purified product was concentrated to an oil (0.66 g) and TFA (30 mL) was added. After an hour stirring, the TFA was evaporated to leave the product as a brown oil which was redissolved in $CH_3CN$ (6 mL) and was purified by HPLC. The pure fractions obtained were combined, concentrated and lyophilised (in t-butanol) to yield a brown oil (0.38 g, 54%).

Purification

HPLC purification:

buffer A: 0.1% $TFA/H_2O$ buffer B: 0.1% TFA+10% $H_2O$+90% $CH_3CN$ 40 mL/min, 214 nm, C18 small prep column Lino-Asp-OH eluted at 55% B, linolenic acid eluted at 65% B, linolenyl-Asp(OtBu)-OtBu eluted at 70% B.

Analysis and Characterisation

1. Analytical HPLC

Buffer A: 0.1% TFA, buffer B: 0.1% TFA/10% $H_2O$/90% $CH_3CN$ 2 mL/min, 214 nm, C18 NovaPak 100% B isocratic, retention times of ingredients:

linolenic acid: Rt 4.14 min linolenyl-Asp(OtBu)-OtBu: Rt 8.46 min linolenyl-Asp-OH: Rt 2.04 min.

2. $^{13}C$ n.m.r.

(DMSO-d6): 14.2, $CH_3$: 20.2,25.26, 25.34, 26.8, 28.69, 28.72, 28.83, 29.2, 35.2. $CH_2$; 36.3, DO; 48.7, Da; 127.1, 127.7, 128.1, 130.1, 131.7, CH; 171.8, 172.2 172.7, C=O.

3. CI-MS m/z 394 (M+1)

Synthesis of Gamma Linolenic Acid-Glycine-OH

γ-linolenic acid, HOSu and H-Gly-OtBu.HCl were dissolved together in DMF (3 mL), the mixture cooled in ice bath and DCC (in 0.3 mL DMF) added. N-MM was added and the mixture stirred for 20 hours, after which time some unreacted linolenic acid remained. More DCC (0.10 g) was added and the mixture stirred for further 20 hours. DCU was filtered off and the product isolated by reverse phase HPLC. The purified product was concentrated to an oil (0.46 g) and TFA (30 mL) was added. After an hour stirring, the TFA was evaporated to leave the product as a brown oil which was redissolved in $CH_3CN$ (6 mL) and was purified by HPLC. The pure fractions obtained were combined, concentrated and lyophilised (in t-butanol) to yield a brown oil (0.35 g, 58%).

Purification

HPLC purification:

buffer A: 0.1% $TFA/H_2O$ buffer B: 0.1% TFA+10% H2O+90% $CH_3CN$ 40 mL/min, 214 nm, C18 small prep column γ-Lino-Gly-OH eluted at 66% B, T-liniolenic acid eluted at 66% B, γ-liilolenvl-Gly-OtBu eluted at 67% B. Compounds eluted in the order listed.

Analysis and Characterisation

1. Analytical HPLC

Buffer A: 0.1% TFA, buffer B: 0.1% TFA/10% $H_2O$/90% $CH_3CN$ 2 mL/min, 214 nm, C18 NovaPak 100% B isocratic, retention times of ingredients:

γ-linolenic acid: Rt 4.07 min

γ-linolenyl-Gly-OtBu: Rt 4.85 min

γ-linolyl-Gly-OH: Rt 2.82 min

2. $^{13}C$ n.m.r.

(DMSO-d6): 14.1, $CH_3$; 22.2,25.0,25.4,26.7,26.8,28.8, 28.9,31.1, 35.1, $CH_2$; 40.7, Ga; 127.7, 127.9, 128.1, 128.2, 129.9, 130.1, CH; 171.6, 172.6, C=O.

3. CI-MS m/z 336 (M+1)

Synthesis of Gamma Linolenic-Aspartic Acid-OH

Gamma linolenic acid, HOSu and H-Asp(OtBu)-OtBu.HCl were dissolved together in DMF (3 mL), the mixture cooled in ice bath and DCC (in 0.3 mL DMF) added. N-MM was added and the mixture stirred for 20 hours, after which time some unreacted linolenic acid remained. More DCC (0.10 g) was added and the mixture stirred for 20 hours, after which time some unreacted linolellic acid remained. More DCC (0.10 g) was added and the mixture stirred for further 20 hours. DCU was filtered off and the product isolated by reverse phase HPLC. The purified product was concentrated to an oil (0.65 g) and TFA (30 mL) was added. After an hour stirring, the TFA was evaporated to leave the product as a brown oil which was redissolved in $CH_3CN$ (6 mL) and was purified by HPLC. The pure fractions obtained were combined, concentrated and lyophilised (in t-butanol) to yield a brown oil (0.30 g. 42%).

Purification

HPLC purification buffer A: 0.1% $TFA/H_2O$

Buffer B: 0.1% TFA+10% $H_2O$+90% $CH_3CN$ 40 mL/min, 214 nm, C18 small prep column Gamma linolenic-Asp-OH eluted at 50% B, linolenic acid eluted at 70% B, linolenyl-Asp(OtBu)-OtBu eluted at 75% B.

Analysis and Characterisation

Buffer A: 0.1% TFA, buffer B: 0.1% TFA/10% $H_2O$/90% $CH_3CN$ 2 mL/min, 214 nm, C18 NovaPak 100% B isocratic, retention times of ingredients:

gamma linolenic acid: Rt 4.14 min gamma linolenyl-Asp(OtBu)-OtBu: Rt 8.71 min gamma linolyl-Asp-OH: Rt 2.28 min 2. $^{13}C$ n.m.r.

(DMSO-d6): 14.1, $CH_3$; 22.2,25.1, 25.4, 26.7,26.8,28.7, 28.9,31.08, 35.1, $CH_2$; 36.3, DP, 48.7, Da; 127.8,127.9, 128.1, 128.2, 130.0, 130.1, CH; 171.9, 172.2, 172.7, C=O.

3. CL-MS m/z 394 (M+1)

Results

TABLE 1

EFFECT OF FATTY ACIDS ON MITOGEN-INDUCED PERIPHERAL BLOOD MONONUCLEAR CELL PROLIFERATION

| COMPOUND | % INHIBITION OF INDUCED PROLIFERATION AT 20 μM PUFA |
|---|---|
| β-oxa 21:3 (n-6) | 17 |
| β-thia 21:3 (n-3) | 28 |
| β-thia 25:6 (n-3) | 97 |
| 16-OH-β-oxa 21:3 (n-6) | 50 |

TABLE 2

EFFECT OF β OXA 23:4 (n-6) ON CALCIUM IMPHORE STIMULATED RELEASE OF LTB$_4$ BY HUMAN NEUTROPHILS.

| Treatment | Imophore stimulated release of LTB$_4$ (pg/well) |
|---|---|
| Control | >40 |
| NDGA (12.5 μM) | 1.25 |
| β oxa 23:4 (n-6) | 2.05 |

Results are from one experiment performed in duplicate and are representative of 4 experiments.

TABLE 3

DTH INDUCED BY SRBC: EFFECT OF PUFA COMPOUND 16-OOH-β-OXA 21:3 (n-6)

| | % paw volume relative to control Time post challenge (hours) | | |
|---|---|---|---|
| | 3 | 6 | 24 |
| Control | 100 | 100 | 100 |
| Prednisolone (20 mg/kg) | 58.35 | 60.12 | 100 |
| Indomethacin (30 mg/kg) | 89.59 | 81.40 | 49.57 |
| 16-OH-β-oxa 21:3 (n-6) | | | |
| 100 mg/kg | 55.86 | 40.94 | 31.97 |
| 50 mg/kg | 65.01 | 48.95 | 51.02 |
| 10 mg/kg | 95.03 | 81.63 | 86.91 |

TABLE 4

EFFECT OF PUFA ON PHA-INDUCED TNFα PRODUCTION

| COMPOUND | % INHIBITION OF CYTOKINE PRODUCTION (PUFA AT 20 μM) |
|---|---|
| β-oxa 21:3 (n-6) | 38 |
| β-oxa 21:3 (n-3) | 39 |
| β-thia 21:3 (n-6) | 17 |
| β-thia 21:3 (n-3) | 17 |
| γ-thia 22:3 (n-6) | 41 |
| γ-thia 22:3 (n-3) | 25 |
| β-oxa 23:4 (n-6) | 25 |
| β-thia 23:4 (n-6) | 35 |
| γ-thia 24:4 (n-6) | 34 |
| β-thia 25:6 (n-3) | 90 |
| 16-OH-β-oxa 21:3 (n-6) | 71 |
| 16-OH-β-oxa 23:4 (n-6) | 68 |

TABLE 5

EFFECT OF PUFA ON *STAPH AUREUS* INDUCED INTERFERON γ PRODUCTION BY PERIPHERAL BLOOD MONONUCLEAR CELLS

| COMPOUND | % INHIBITION (PUFA AT 20 μM) |
|---|---|
| β-oxa 21:3 (n-6) | 89 |
| β-thia 21:3 (n-6) | 45 |
| β-oxa 25:6 (n-3) | 44 |
| β-oxa 23:4 (n-6) | 89 |
| β-thia 23:4 (n-6) | 64 |
| β-thia 25:6 (n-6) | 96 |
| 16-OH-β-oxa 21:3 (n-6) | 77 |
| 16-OH-β-oxa 23:4 (n-6) | 65 |

TABLE 6

EFFECT OF AMINO ACID CONJUGATED PUFAS ON PHA-STIMULATED TNFα AND INTERFERON γ PRODUCTION

| COMPOUND | % inhibition of TNFα production | % inhibition of IFNγ production |
|---|---|---|
| α-linolenic acid-glycine | 29.3 | 14.5 |
| α-linolenic acid-aspartic acid | 0 | 0 |
| γ-linolenic acid-glycine | 21.5 | 0 |
| γ-linolenic acid-aspartic acid | 4.7 | 0 |
| arachidonic acid-glycine | 26.6 | 35.9 |
| arachidonic acid-aspartic acid | 38.3 | 68.4 |
| eicosapentanoic acid-glycine | 11 | 68.2 |
| eicosapentanoic acid-aspartic acid | 17.1 | 66.1 |
| docosahexanoic acid-glycine | 16.2 | 44 |
| docosahexanoic acid-aspartic acid | 17.4 | 8.3 |

All PUFA were at 20 μM

All PUFA were at 20 μM

TABLE 7

EFFECT OF PUFA ON CELL PROLIFERATION INDUCED BY PHA

| COMPOUND | % INHIBITION OF PROLIFERATION |
|---|---|
| α-linolenic acid-glycine | 15.6 |
| α-linolenic acid-aspartic acid | 7.3 |
| γ-linolenic acid-glycine | 29 |
| γ-linolenic acid-aspartic acid | 15.4 |
| arachidonic acid-glycine | 8 |
| arachidonic acid-aspartic acid | 39/7 |
| eicosapentanoic acid-glycine | 5.4 |
| eicosapentanoic acid-aspartic acid | 20.7 |
| docosahexanoic acid-glycine | 16.6 |
| docosahexanoic acid-aspartic acid | 21.1 |

All PUFA were at 20 μM

All PUFA were at 20 μM

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

What is claimed is:

1. A method of treating or ameliorating symptoms of T-cell mediated disease in a subject, the method comprising administering to the subject a composition comprising a therapeutically effective amount of a polyunsaturated fatty acid and a pharmaceutically acceptable carrier; in which the polyunsaturated fatty acid contains 18–25 carbons, 1–6 double bonds and has one or two substitutions selected from the group consisting of β oxa, γ oxa, β thia and γ thia, based on the fatty acid acyl carbon, wherein said T-cell mediated disease is selected from the group consisting of diabetes multiple sclerosis, rheumatoid arthritis, herpes simplex, stromal keratitis, psoriasis, Crohn's disease, inflammatory bowel disease, graft vs. host disease, scleroderma, asthma, rhinitis, eczema, atoptic dermatitis, allergic diseases, systemic lupus, erythematosis and polymyositis.

2. A method as claimed in claim 1 in which T-cell mediated disease is multiple sclerosis.

3. A method as claimed in claim 1 in which T-cell mediated disease is rheumatoid arthritis.

4. A method of treating or ameliorating symptoms of a disease state involving elevated levels of products of arachidonic acid metabolism in a subject, the method comprising administering to the subject a composition comprising a therapeutically effective amount of a polyunsaturated fatty acid and a pharmaceutically acceptable carrier; in which the polyunsaturated fatty acid contains 18–25 carbons, 1–6 double bonds and has one or two substitutions selected from the group consisting of β oxa, γ oxa, β thia and γ thia, based on the fatty acid acyl carbon, wherein said disease state is selected from the group consisting of adult respiratory distress syndrome (ARDS), cystic fibrosis, psoriasis, allergic asthma, rhinitis, leukoclastic vasculitis, urticaria and angioedema.

5. A method as claimed in claim 4 in which the a disease state involving elevated levels of products of arachidonic acid metabolism is psoriasis.

6. A method as claimed in claim 4 in which the a disease state involving elevated levels of products of arachidonic acid metabolism is asthma.

7. A method as claimed in claim 1 in which the polyunsaturated fatty acid includes a further substitution selected from the group consisting of hydroxy, hydroperoxy, peroxy and carboxymethyl substitutions.

8. A method as claimed in claim 1 in which the polyunsaturated fatty acid has a ω hydroxy substitution.

9. A method as claimed in claim 1 in which the polyunsaturated fatty acid compound contains 20–25 carbon atoms and 3–6 double bonds.

10. A method as claimed in claim 1 in which the polyunsaturated fatty acid contains 20 carbon atoms with 3–4 double bonds containing a β oxa or β thia substitution, 21 carbon atoms with 3–4 double bonds containing a β oxa, β thia or γ thia substitution, 22 carbon atoms with 3–5 double bonds containing a β oxa a thia or γ thia substitution, 23 carbon atoms with 3–5 double bonds containing a β oxa, β thia or γ thia substitution, 24 carbon atoms with 3–6 double bonds containing a β oxa, β thia or γ thia substitution, 25 carbon atoms with 3–6 double bonds containing a β oxa, β thia or γ thia substitution, or 20–24 carbon atoms with 3–6 double bonds, containing a β thia and α-carboxymethyl group.

11. A method as claimed in claim 1 in which the T-cell mediated disease is lupus.

12. A method as claimed in claim 9 in which the polyunsaturated fatty acid compound is an n-3 to n-6 fatty acid.

13. A method as claimed in claim 1, wherein the T-cell mediated disease is selected from the group consisting of multiple sclerosis, rheumatoid arthritis, herpes simplex, stromal keratitis, Crohn's disease, inflammatory bowel disease, graft vs host disease, sclerodoma, allergic disease and polymyocitis.

* * * * *